United States Patent
Schneider et al.

(10) Patent No.: US 10,086,049 B2
(45) Date of Patent: Oct. 2, 2018

(54) CONJUGATES OF SOMATOSTATIN ANALOGUES

(71) Applicant: ProLynx LLC, San Francisco, CA (US)

(72) Inventors: Eric L. Schneider, Oakland, CA (US); Brian Hearn, Lafayette, CA (US); Gary W. Ashley, Alameda, CA (US); Daniel V. Santi, San Francisco, CA (US)

(73) Assignee: ProLynx LLC, San Francisco, CA (US)

( * ) Notice: Subject to any disclaimer, the term of this patent is extended or adjusted under 35 U.S.C. 154(b) by 0 days.

(21) Appl. No.: 15/030,353

(22) PCT Filed: Oct. 22, 2014

(86) PCT No.: PCT/US2014/061844
§ 371 (c)(1),
(2) Date: Apr. 18, 2016

(87) PCT Pub. No.: WO2015/061503
PCT Pub. Date: Apr. 30, 2015

(65) Prior Publication Data
US 2016/0271227 A1    Sep. 22, 2016

Related U.S. Application Data

(60) Provisional application No. 61/894,226, filed on Oct. 22, 2013.

(51) Int. Cl.
| | | |
|---|---|---|
| A61K 38/31 | (2006.01) | |
| A61K 47/48 | (2006.01) | |
| A61K 47/60 | (2017.01) | |
| A61K 47/69 | (2017.01) | |

(52) U.S. Cl.
CPC .............. *A61K 38/31* (2013.01); *A61K 47/60* (2017.08); *A61K 47/6903* (2017.08)

(58) Field of Classification Search
None
See application file for complete search history.

(56) References Cited

U.S. PATENT DOCUMENTS

| | | |
|---|---|---|
| 7,803,773 B2 | 9/2010 | Kuzma et al. |
| 7,960,335 B2 | 6/2011 | Kuzma et al. |
| 8,640,315 B1 | 2/2014 | Nikkel et al. |
| 8,703,907 B2 | 4/2014 | Ashley et al. |
| 8,754,190 B2 | 6/2014 | Ashley et al. |
| 2008/0292712 A1 | 11/2008 | Lewis et al. |
| 2013/0123487 A1 | 5/2013 | Ashley et al. |

FOREIGN PATENT DOCUMENTS

| | | |
|---|---|---|
| WO | WO-2009/158668 | 12/2009 |
| WO | WO-2011/085957 | 7/2011 |
| WO | WO-2011/140392 | 11/2011 |
| WO | WO-2013/036847 | 3/2013 |
| WO | WO-2013/083459 | 6/2013 |

OTHER PUBLICATIONS

Boyd et al., "Lyotropic liquid crystalline phases formed from glycerate surfactants as sustained release drug delivery systems," Int J Pharm (2006) 309(1-2):218-226.
Ghassemi et al., "Controlled release of octreotide and assessment of peptide acylation from poly(D,L-lactide-co-hydroxymethyl glycolide) compared to PLGA microspheres," Pharm Res (2012) 29(1):110-120.
International Preliminary Report on Patentability for PCT/US2014/061844, dated May 6, 2016, 7 pages.
International Search Report and Written Opinion for PCT/US2014/061844, dated Jan. 9, 2015, 9 pages.
Supplementary European Search Report for EP 14856508.8, dated May 12, 2017, 7 pages.

*Primary Examiner* — Thomas S Heard
(74) *Attorney, Agent, or Firm* — Morrison & Foerster LLP

(57) ABSTRACT

Conjugates of carriers and hydrogels for controlling the biological half-life of somatostatin and its analogs are disclosed.

1 Claim, 12 Drawing Sheets

Octreotide N$_\alpha$-linked conjugate

Octreotide N$_\alpha$-linked conjugate

Octreotide N$_\alpha$-amide-linked conjugate

Preparation of azide-linker-OSu and MMT-amide-linker-OSu

Preparation of N$_\alpha$-linked azide-linker-octreotide

Preparation of N$_\alpha$-linked Azide-linker-octreotide

Preparation of N$_\alpha$-linked amine-Linker-Octreotide conjugate

*In vitro* release kinetics

Preparation of a somatostatin-analog hydrogel

Preparation of an amide-connected octreotide hydrogel macromonomer.

CONJUGATES OF SOMATOSTATIN ANALOGUES

CROSS-REFERENCE TO RELATED APPLICATIONS

This application is the national phase of PCT application PCT/US2014/061844 having an international filing date of 22 Oct. 2014, which claims benefit of U.S. provisional patent application No. 61/894,226 filed 22 Oct. 2013. The contents of the above patent applications are incorporated by reference herein in their entirety.

TECHNICAL FIELD

The invention is in the field of formulation of medicaments for extension of half-life.

BACKGROUND ART

Somatostatin is a peptide hormone that regulates the endocrine system and affects neurotransmission and cell proliferation via interaction with G-protein coupled receptors that results in the inhibition of release of several secondary hormones, including growth hormone and thyroid-stimulating hormone (TSH) in the anterior pituitary; gastrin, cholecystokinin, motilin, glucagon, secretin, pancreatic polypeptide, thyroid stimulating hormone (TSH), gastric inhibitory peptide (GIP), enteroglucagon, and vasoactive intestinal peptide (VIP) in the gastrointestinal system; and insulin and glucagon in the pancreas.

Several synthetic analogs of somatostatin are known, including octreotide, lanreotide, and pasireotide.

Octreotide (D-phenylalanyl-L-cysteinyl-L-phenylalanyl-D-tryptophyl-L-lysyl-L-threonyl-N-[2-hydroxy-1-(hydroxymethyl)propyl]-L-Cysteinamide, cyclic (2→7)-disulfide; [R—(R*,R*)]) is a synthetic octapeptide mimic of the natural peptide somatostatin. It inhibits the secretion of many hormones, including gastrin, cholecystokinin, glucagon, growth hormone, insulin, secretin, pancreatic polypeptide, thyroid stimulating hormone (TSH), and vasoactive intestinal peptide (VIP). It decreases gastric motility, inhibits contraction of the gallbladder, reduces fluid secretion by the intestines and pancreas, causes vasoconstriction, and reduces portal pressures in bleeding varices. It has been shown to produce analgesic effects, possibly through activity at the mu-opioid receptor. The acetate salt has been approved for use in the USA as an injectable depot formulation for treatment of acromegaly, gigantism, thyrotropinoma, diarrhea and flushing associated with carcinoid syndrome, and diarrhea in patients suffering from VIP-secreting tumors. It has been used off-label for treatment of a number of afflictions, including severe refractory diarrhea, prolonged recurrent hypoglycemia after sulfonylurea overdose, insulin hypersecretion in infants with nesidioblastosis, hypertrophic pulmonary osteoarthropathy secondary to non-small cell lung cancer, malignant bowel obstruction, and chronic hypotension.

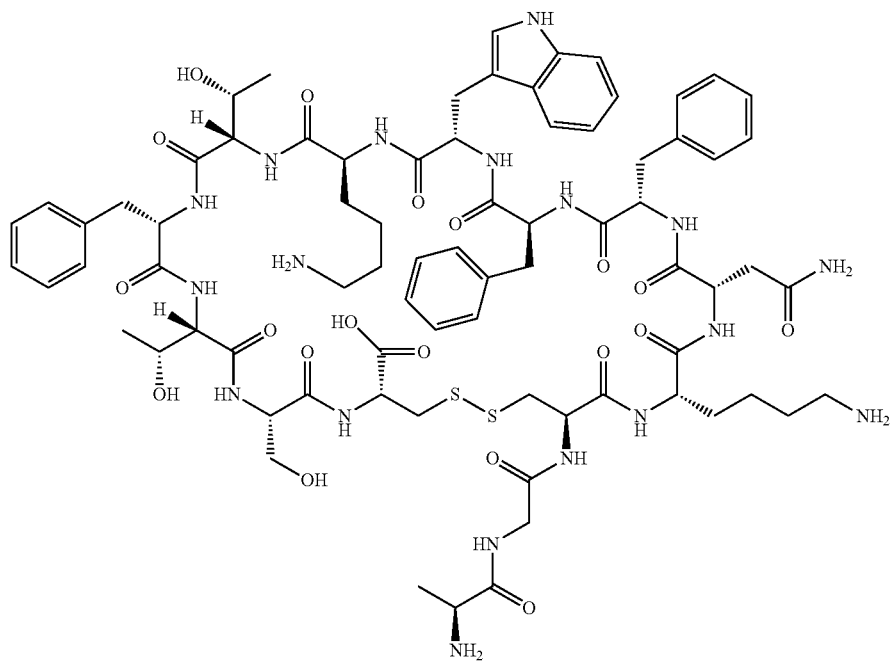

somatostatin

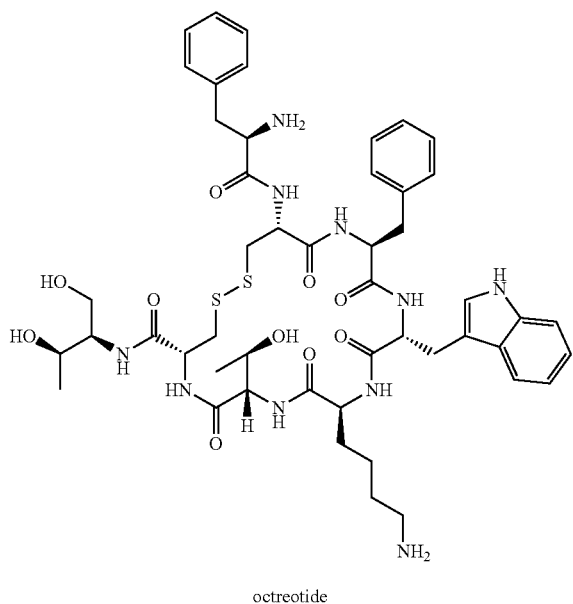 [SMILES: C[C@@H](O)[C@@H]1NC(=O)[C@H](CCCCN)NC(=O)[C@@H](Cc2c[nH]c3ccccc23)NC(=O)[C@H](Cc2ccccc2)NC(=O)[C@@H](NC(=O)[C@H](N)Cc2ccccc2)CSSC[C@@H](C(=O)N[C@H](CO)[C@@H](C)O)NC1=O]

octreotide

Octreotide has been used experimentally in the treatment of obesity, chronic pain resulting from pancreatitis, thymic neoplasms, and idiopathic intracranial hypertension.

It has been noted that octreotide alters the balance between the counter-regulatory hormones insulin, glucagon, and growth hormone, and so may cause hypo- or hyperglycemia. This was observed in acromegalic patients (3% and 16%, respectively), but only at 1.5% in other patient populations.

An immediate-release formulation known as Sandostatin® Injection (Novartis) is self-administered 2 to 4 times daily by subcutaneous injection. Each dose comprises 50, 100, or 500 ug of octreotide acetate formulated with lactic acid, mannitol, and sodium bicarbonate in water at pH 4.2. Initial doses of 50 ug may be upwardly titrated depending on need. After injection of a 100 ug dose, peak concentrations of 5.2 ng/mL were reached. Octreotide is absorbed quickly after subcutaneous administration, and is eliminated from the plasma with an average half-life of 1.7 h; the duration of action is variable but extends up to 12 h.

A microsphere formulation known as Sandostatin LAR® Depot comprises octreotide acetate and mannitol encapsulated in a poly(D,L-lactide-co-glycolide) (PLGA) glucose star polymer, in strengths of 10, 20, or 30 mg of octreotide acetate. The suspension resulting from dilution of the dry microspheres with aqueous carboxymethylcellulose sodium and mannitol is given by a trained health care provider as a monthly intragluteal injection using a 1.5-2" 19 gauge needle. The microspheres degrade over time through hydrolysis of the copolymer matrix, releasing the octreotide. As the microspheres are unstable in water, the suspension must be carefully prepared and administered immediately after mixing. With multiple monthly dosing, a steady-state level of free octreotide is attained after 3 doses. Dosing 20 mg results in trough levels of 1.2 ng/mL and peak levels of 1.6 ng/mL; dosing 30 mg results in trough levels of 2.1 ng/mL and peak levels of 2.6 ng/mL. Extensive degradation of octreotide in Sandostatin LAR® due to amine acylation by polymer units has been reported (Ghassemi, et al., "Controlled Release of Octreotide and Assessment of Peptide Acylation from Poly(D,L-lactide-co-hydroxymethyl glycolide) Compared to PLGA Microspheres," Pharm. Res. (2012) 29:110-120). The low pH environment inside PLGA microspheres appears to be detrimental to peptide stability, and thus limits their use as long-term delivery agents for peptides.

Liquid crystal phase depot formulations of octreotide have been recently reported, for example in PCT Publication WO2013/083459 A1 and Boyd, et al., "Lyotropic liquid crystalline phases formed from glycerate surfactants as sustained release drug delivery systems," Int. J. Pharm. (2006) 309:218-226. Formulations having octreotide non-covalently entrapped within a hydrogel matrix and which may be delivered via a subcutaneous implant have also been disclosed (for example, in U.S. Pat. Nos. 7,803,773 and 7,960,335).

Lanreotide ([3-(2-naphthyl)-D-alanyl-L-cysteinyl-L-tyrosyl-D-tryptophyl-L-lysyl-L-valyl-L-cysteinyl-L-threoninamide cyclic (3→7)-disulfide) has a longer half-life after administration, and is available in two formulations, Somatuline® LA requiring intramuscular injection every 10-14 days and Somatuline® Depot (Somatuline® Autogel in the UK) that is administered deep subcutaneous once a month. Somatuline® Depot comprises lanreotide acetate in supersaturated aqueous semisolid formulation at 60, 90, or 120 mg. Upon deep intramuscular injection, it is thought to form a precipitated drug depot that slowly releases lanreotide with a half-life of 23-30 days. At steady-state after multiple dosing, the mean trough concentrations were 1.8, 2.5, and 3.8 ng/mL at 60, 90, and 120 mg doses, and mean peak concentrations were 3.8, 5.7, and 7.7 ng/mL.

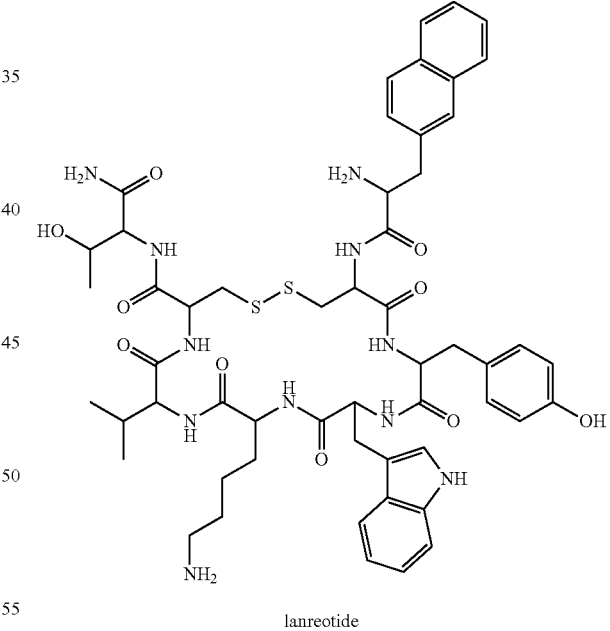

lanreotide

Pasireotide ((2-aminoethyl) carbamic acid (2R,5S,8S,11S,14R,17S,19aS)-11-(4-aminobutyl)-5-benzyl-8-(4-benzyloxybenzyl)-14-(1H-indol-3ylmethyl)-4,7,10,13,16,19-hexaoxo-17-phenyloctadecahydro-3a,6,9,12,15,18-hexaazacyclopentacyclooctadecen-2-yl ester, di[(S)-2-aminosuccinic acid] salt) is an orphan drug approved in the U.S. and Europe for the treatment of Cushing's disease in patients who fail or are ineligible for surgical therapy. It has a 40-fold increased affinity to somatostatin receptor 5 than other somatostatin analogs.

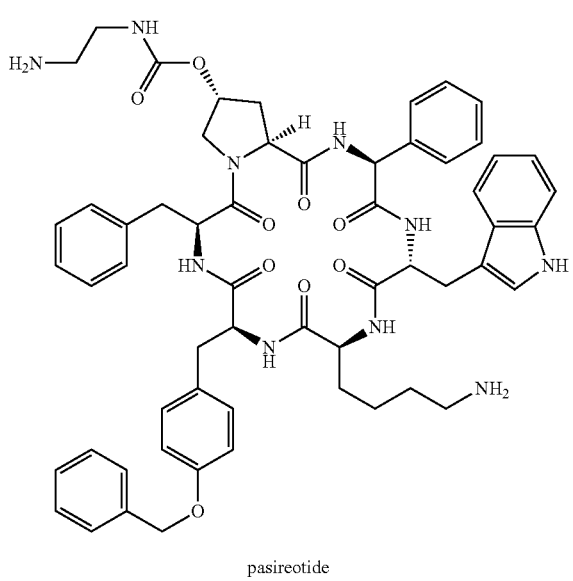 [SMILES: NCCCC[C@@H]1NC(=O)[C@@H](Cc2c[nH]c3ccccc23)NC(=O)[C@H](c2ccccc2)NC(=O)[C@@H]2C[C@@H](OC(=O)NCCN)CN2C(=O)[C@H](Cc2ccccc2)NC(=O)[C@H](Cc2ccc(OCc3ccccc3)cc2)NC1=O]

pasireotide

Pasireotide is marketed as Signifor® (Novartis) in a formulation comprising pasireotide diaspartate at 0.3, 0.6, or 0.9 mg, mannitol, tartaric acid, and water at pH 4.2. Upon subcutaneous administration, it shows a large volume of distribution (>100 L) and an effective half-life of approximately 12 h.

Formulations that have been used for other drugs and that are related to the problems solved in the present invention have been disclosed, for example, in U.S. Pat. No. 8,640,315 which describes linkers wherein the drug is bound to a system for β-elimination through a linkage of the formula —X—C(O)-D, where D is the drug, and the linker couples the drug to a macromolecule.

U.S. Pat. No. 8,754,190 alters the formulation for coupling the drug to that of the formula —O—C(O)—N(B)—CH$_2$-D where, again, D represents a drug and the drug is coupled through a β-elimination linker to a macromolecule.

WO2011/140392 describes similar linkers using both of the aforementioned types of coupling to the drug to link the drug to a solid support. U.S. Pat. No. 8,703,907 uses both types of linkage to the drug to couple the drug through a linker to a dendrimer.

WO2013/036847 describes similar linkages where the linker is coupled to an optionally crosslinked hydrogel. None of these delivery systems is designed specifically to be adapted to appropriate delivery of effective amount of somatostatin or its analogs.

Given the often painful intramuscular or deep subcutaneous injections requiring administration by trained healthcare professionals, and the instability of peptide drugs in PLGA microspheres, there exists a need for improved methods of administering these useful therapeutic agents.

DISCLOSURE OF THE INVENTION

The present invention solves problems associated with administration of somatostatin and its analogs related to sufficient dosage, sufficient solubility of formulations, and a mechanism for controlled release so that long-lasting administration can be achieved. Typically, in order to provide sufficient dosage of the somatostatin or its analog, multiple copies of the drug need to be included in the slow-release formulation. The invention provides means to do this either by providing multiple copies of the somatostatin or its analog in a hydrogel which can be provided in an insoluble, depot form, or by providing multiple copies on a soluble multi-armed macromolecule. In both cases, the somatostatin or analog is coupled to the hydrogel or to the multi-armed polymer through a linker that provides controlled release using a β-elimination reaction.

The present invention thus provides conjugates that allow for controlled release of somatostatin and its analogs and improved means of administration. The conjugates of the invention may be soluble, acting as a long-lived circulating source of the peptide, or they may be insoluble, acting as a non-circulating depot. The present invention also provides methods for preparing these conjugates and methods for their use. The conjugates of the invention are expected to find utility in the treatment of diseases and conditions wherein treatment with somatostatin or analog is already known to be useful.

In one aspect of the invention, soluble conjugates of a somatostatin and its analog having controlled release are provided. The soluble conjugates of the invention are of the formula (1)

$$P\text{-}(L\text{-}D)_n \quad (1)$$

wherein P is a carrier molecule or a hydrogel, L is a releasable linker capable of releasing D through a beta-elimination reaction, D is somatostatin or its analog, i.e., somatostatin or an analog thereof, and n=1-8 when P is a carrier molecule and a multiplicity when P is a hydrogel.

In more detail, the invention is directed to a conjugate including a derivatized hydrogel of the formula (1)

$$P\text{-}(L\text{-}D)_n \quad (1)$$

wherein P is a carrier molecule or a hydrogel;
D is somatostatin or its analog;
n=1-8 when P is a carrier molecule and a multiplicity when P is a hydrogel; and
L is a moiety of formula (2)

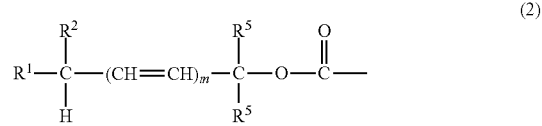

wherein in formula (2) m=0 or 1;
at least one or both $R^1$ and $R^2$ is independently CN; or
NO$_2$; or
optionally substituted aryl; or
optionally substituted heteroaryl; or
optionally substituted alkenyl; or
optionally substituted alkynyl; or
COR$^3$ or SOR$^3$ or SO$_2$R$^3$ wherein
  R$^3$ is H or optionally substituted alkyl;
  aryl or arylalkyl, each optionally substituted;
  heteroaryl or heteroarylalkyl, each optionally substituted; or
  OR$^9$ or NR$^9{}_2$ wherein each R is independently H or optionally substituted alkyl, or both R$^9$ groups taken together with the nitrogen to which they are attached form a heterocyclic ring; or
SR$^4$ wherein
  R$^4$ is optionally substituted alkyl;
  aryl or arylalkyl, each optionally substituted; or
  heteroaryl or heteroarylalkyl, each optionally substituted; or wherein R¹ and R² are joined to form a 3-8 membered ring; and wherein one and only one of R¹ and R² may be H or may be alkyl, arylalkyl or heteroarylalkyl, each optionally substituted; and each $R^5$ is independently H or is alkyl, alkenylalkyl, alkynylalkyl, $(CH_2CH_2O)_p$ wherein p=1-1000, aryl, arylalkyl, heteroaryl or heteroarylalkyl, each optionally substituted; and wherein one of R¹, R², or $R^5$ is connected to P or to the hydrogel.

The "multiplicity" noted by "n" when P is a hydrogel is typically a large number, determined at least in part by the number of macromonomers in the hydrogel. In one embodiment, each drug-bearing macromonomer contains at least 4 copies of the linked somatostatin or analog. Because the hydrogels can be of a variety of sizes, specifying a specific number of linked somatostatin or analog moieties does not really make sense. The dimensions of the hydrogel could be, for instance, 1 μl or 100 μl or larger. In general, n is therefore a large number.

Insoluble hydrogel conjugates of a somatostatin or its analog having controlled release are included, as well as soluble conjugates. The invention is also directed to precursors for the drug delivery systems of the invention, including compounds which comprise somatostatin or its analog coupled to a suitable linker. The hydrogels may be cross-linked using the same type of linker that is cleavable by n-elimination.

The invention also relates to methods of treatment using the drug delivery system of the invention. Thus, the invention is also directed to methods to treat conditions benefited by somatostatin and its analogs by administering them in the form of the invention conjugates including hydrogels.

MODES OF CARRYING OUT THE INVENTION

Figure 1:
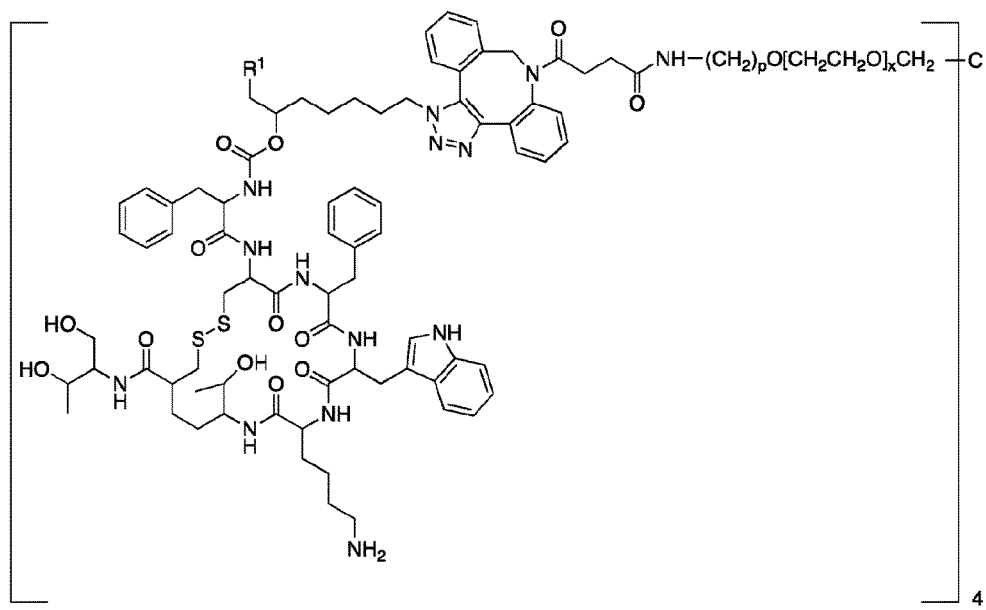
FIG. 1 illustrates a soluble conjugate of the invention wherein octreotide is releasably linked using a DBCO-derived triazole to a 4-arm PEG via the alpha-amine.

The term "somatostatin analog" encompasses somatostatin and peptidic analogs thereof, including octreotide, lanreotide, and pasireotide. Thus although "somatostatin analog" is sometimes used for economy of verbiage, this term means somatostatin or its analogs.

The term "PEG" is meant to encompass linear, branched, or multi-arm polymers of ethylene oxide having average molecular weights between 10,000 and 100,000 comprising at least one functional group Z that allows for covalent attachment of a releasable linker. Suitable functional groups Z include amines; alkoxyamines; ketones; aldehydes; carboxylates; active esters such as N-hydroxysuccinimide esters, nitrophenyl esters, and pentahalophenyl esters; active carbonates and carbamates; thiols; maleimides; azides; terminal alkynes; strained cyclooctynes; trans-cyclooctenes; cyclopropenes; norbornenes; tetrazines; nitrile oxides; cyclopentadienes; and furans.

By the term "hydrogel" is meant an insoluble cross-linked network of hydrophilic polymer chains. The hydrogel may be comprised of one or more synthetic or natural polymers, including PEG, polyacrylamide, hyaluronate, dextran, or similar polymers.

By the term "conjugate" is meant a compound prepared by the covalent attachment of a somatostatin or its analog to a carrier molecule or to a derivatized hydrogel, wherein the carrier molecule or hydrogel serves to extend the lifetime of the somatostatin or its analog in vivo. The carrier molecule may be biologically inactive with respect to the condition or disease being treated with the conjugate or may serve to direct the therapeutic agent to a particular target or tissue relevant to the condition or disease.

By the term "beta-elimination" is meant a chemical reaction through which a compound comprising the substructure CH—(CH=CH)$_m$—CX, where m=0-1, is converted into a compound comprising the substructure C=(C—C)$_m$=C through loss of the elements of H—X.

By the term "substituted" is meant an alkyl, alkenyl, alkynyl, aryl, or heteroaryl group comprising one or more substituent groups in place of one or more hydrogen atoms. Substituent groups may generally be selected from halogen including F, Cl, Br, and I; lower alkyl including linear, branched, and cyclic; lower haloalkyl including fluoroalkyl, chloroalkyl, bromoalkyl, and iodoalkyl; OH; lower alkoxy including linear, branched, and cyclic; SH; lower alkylthio including linear, branched, and cyclic; amino, alkylamino, dialkylamino, silyl including alkylsilyl, alkoxysilyl, and arylsilyl; nitro; cyano; carbonyl; carboxylic acid, carboxylic ester, carboxylic amide; aminocarbonyl; aminoacyl; carbamate; urea; thiocarbamate; thiourea; ketone; sulfone; sulfonamide; aryl including phenyl, naphthyl, and anthracenyl; heteroaryl including 5-member heteroaryls including as pyrrole, imidazole, furan, thiophene, oxazole, thiazole, isoxazole, isothiazole, thiadiazole, triazole, oxadiazole, and tetrazole, 6-member heteroaryls including pyridine, pyrimidine, pyrazine, and fused heteroaryls including benzofuran, benzothiophene, benzoxazole, benzimidazole, indole, benzothiazole, benzisoxazole, and benzisothiazole.

The terms "alkyl", "alkenyl", and "alkynyl" include linear, branched or cyclic hydrocarbon groups of 1-8 carbons or 1-6 carbons or 1-4 carbons wherein alkyl is a saturated hydrocarbon, alkenyl includes one or more carbon-carbon double bonds and alkynyl includes one or more carbon-carbon triple bonds. Unless otherwise specified these contain 1-6C.

The term "aryl" includes aromatic hydrocarbon groups of 6-18 carbons, preferably 6-10 carbons, including groups such as phenyl, naphthyl, and anthracenyl. The term "heteroaryl" includes aromatic rings comprising 3-15 carbons containing at least one N, O or S atom, preferably 3-7 carbons containing at least one N, O or S atom, including groups such as pyrrolyl, pyridyl, pyrimidinyl, imidazolyl, oxazolyl, isoxazolyl, thiazolyl, isothiazolyl, quinolyl, indolyl, indenyl, and similar.

The term "halogen" includes fluoro, chloro, bromo and iodo.

The term "maleimido" is a group of the formula

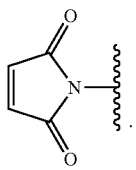

By the term "releasable linker" is meant a moiety that covalently connects the somatostatin or its analog to the carrier molecule or hydrogel in a conjugate, and which is capable of releasing the therapeutic molecule from the carrier molecule or hydrogel under defined conditions. In the conjugates of the present invention, the releasable linker is capable of releasing the somatostatin or its analog through a beta-elimination reaction. Thus, the releasable linkers of the invention may be described by formula (2)

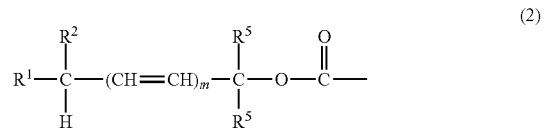

$R^1$ and $R^2$ are independently CN; $NO_2$; optionally substituted aryl; optionally substituted heteroaryl; optionally substituted alkenyl; optionally substituted alkynyl; $COR^3$ or $SOR^3$ or $SO_2R^3$ wherein $R^3$ is H or optionally substituted alkyl; aryl or arylalkyl, each optionally substituted; heteroaryl or heteroarylalkyl, each optionally substituted; or $OR^9$ or $NR^9_2$ wherein each $R^9$ is independently H or optionally substituted alkyl, or both $R^9$ groups taken together with the nitrogen to which they are attached form a heterocyclic ring; $SR^4$ wherein $R^4$ is optionally substituted alkyl; aryl or arylalkyl, each optionally substituted; or heteroaryl or heteroarylalkyl, each optionally substituted; or wherein $R^1$ and $R^2$ may be joined to form a 3-8 membered ring. One and only one of $R^1$ and $R^2$ may be H or may be alkyl, arylalkyl or heteroarylalkyl, each optionally substituted.

As described in PCT Publication WO2009/158668 A1, the electronic properties of $R^1$ and $R^2$ are the primary determinants of the rate of release from the linker. The properties of $R^1$ and $R^2$ may be modulated by the optional addition of electron-donating or electron-withdrawing substituents. By the term "electron-donating group" is meant a substituent resulting in a decrease in the acidity of the $R^1R^2$CH; electron-donating groups are typically associated with negative Hammett s or Taft s* constants and are well-known in the art of physical organic chemistry. (Hammett constants refer to aryl/heteroaryl substituents, Taft constants refer to substituents on non-aromatic moieties.) Examples of suitable electron-donating substituents include but are not limited to lower alkyl, lower alkoxy, lower alkylthio, amino, alkylamino, dialkylamino, and silyl. Similarly, by "electron-withdrawing group" is meant a substituent resulting in an increase in the acidity of the $R^1R^2$CH group; electron-withdrawing groups are typically associated with positive Hammett s or Taft s* constants and are well-known in the art of physical organic chemistry. Examples of suitable electron-withdrawing substituents include but are not limited to halogen, difluoromethyl, trifluoromethyl, nitro, cyano, C(=O)—$R^X$, wherein $R^X$ is H, lower alkyl, lower alkoxy, or amino, or $S(O)_mR^Y$, wherein m=1-2 and $R^Y$ is lower alkyl, aryl, or heteroaryl. As is well-known in the art, the electronic influence of a substituent group may depend upon the position of the substituent. For example, an alkoxy substituent on the ortho- or para-position of an aryl ring is electron-donating, and is characterized by a negative Hammett s constant, while an alkoxy substituent on the meta-position of an aryl ring is electron-withdrawing and is characterized by a positive Hammett s constant. A table of Hammett s and Taft s* constants values is given below.

| Substituent | σ (meta) | σ (para) | σ* |
|---|---|---|---|
| H | 0.00 | 0.00 | 0.49 |
| $CH_3$ | −0.07 | −0.17 | 0 |
| $C_2H_5$ | −0.07 | −0.15 | −0.10 |
| n-$C_3H_7$ | −0.07 | −0.13 | −0.115 |
| i-$C_3H_7$ | −0.07 | −0.15 | −0.19 |
| n-$C_4H_9$ | −0.08 | −0.16 | −0.13 |
| t-$C_4H_9$ | −0.10 | −0.20 | −0.30 |

-continued

| Substituent | σ (meta) | σ (para) | σ* |
|---|---|---|---|
| $H_2C=CH$ | 0.05 | −0.02 | |
| $C_6H_5$ | 0.06 | −0.01 | 0.60 |
| $CH_2Cl$ | 0.11 | 0.12 | 1.05 |
| $CF_3$ | 0.43 | 0.54 | |
| CN | 0.56 | 0.66 | |
| CHO | 0.35 | 0.42 | |
| $COCH_3$ | 0.38 | 0.50 | |
| $CO_2H$ | 0.37 | 0.45 | |
| $Si(CH_3)_3$ | −0.04 | −0.07 | |
| F | 0.34 | 0.06 | |
| Cl | 0.37 | 0.23 | |
| Br | 0.39 | 0.23 | |
| I | 0.35 | 0.18 | |
| OH | 0.12 | −0.37 | |
| $OCH_3$ | 0.12 | −0.27 | |
| $OCH_2CH_3$ | 0.10 | −0.24 | |
| SH | 0.25 | 0.15 | |
| $SCH_3$ | 0.15 | 0.00 | |
| $NO_2$ | 0.71 | 0.78 | |
| NO | 0.62 | 0.91 | |
| $NH_2$ | −0.16 | −0.66 | |
| NHCHO | 0.19 | 0.00 | |
| $NHCOCH_3$ | 0.07 | −0.15 | |
| $N(CH_3)_2$ | −0.15 | −0.83 | |
| $N(CH_3)^+$ | 0.88 | 0.82 | |
| $CCl_3$ | | | 2.65 |
| $CO_2CH_3$ | | | 2.00 |
| $CH_2NO_2$ | | | 1.40 |
| $CH_2CF_3$ | | | 0.92 |
| $CH_2OCH_3$ | | | 0.52 |
| $CH_2Ph$ | | | 0.26 |

In embodiments of the invention, m=0-1. In particular embodiments, m=0.

Each $R^5$ is independently H or is alkyl, alkenylalkyl, alkynylalkyl, $(CH_2CH_2O)_p$ wherein p=1-1000, aryl, arylalkyl, heteroaryl or heteroarylalkyl, each optionally substituted; and wherein one $R^5$ further comprises a functional group Z allowing for connection to a macromolecular carrier.

In one aspect of the invention, soluble conjugates of somatostatin or a somatostatin analog having controlled release are provided. The soluble conjugates of the invention are of the formula (1)

P-(L-D)$_n$ (1)

wherein P is a soluble carrier molecule or is a hydrogel, L is a releasable linker capable of releasing D through a beta-elimination reaction as described above, D is somatostatin or its analog, and n=1-8 when P is a carrier molecule. When P is a hydrogel, n is a larger number dependent on the number of macromolecular units in the gel.

In various embodiments of the invention, the somatostatin or its analog D is connected to the releasable linker L through a carbamate linkage to an amine group on D. In certain embodiments of the invention, D is connected to L through the N-terminal alpha-$NH_2$ group. In other embodiments of the invention, D is connected to L through the epsilon-$NH_2$ group of a lysine residue. In yet other embodiments of the invention, D is connected to L through the $NH_2$ group of a 2-aminoethyl-carbamate group.

In embodiments of the invention, the releasable linker L is connected to P using a functional group Z on one of $R^1$, $R^2$, or $R^5$ of the releasable linker and a cognate functional group $Z^*$ on P. Examples of cognate pairs of functional groups Z/$Z^*$ are given in Table 1 below. It will be recognized that the positions of Z and $Z^*$ may be reversed.

TABLE 1

Selected pairs of reactive functional groups

| | | |
|---|---|---|
| Azide | + | acetylene, cyclooctyne, maleimide |
| Thiol | + | maleimide, acrylate, acrylamide, vinylsulfone, halogen |
| Amine | + | carboxylate, active ester |
| Maleimide | + | thiol, azide, 1,3-diene, furan, cyclopentadiene |
| Tetrazine | + | cyclopropene, norbornene, trans-cyclooctene |
| R—C=O | + | amino-ether |

P will comprise at least one functional group $Z^*$ (or Z) allowing for attachment of a reversible linker as discussed above. The $Z^*$ (or Z) group may be naturally occurring in P or may be added by chemical derivatization using methods well known in the art of conjugation.

When P is a soluble carrier molecule, P may be a synthetic or natural polymer, such as a poly(ethylene glycol) (PEG), dextran, hyaluronic acid, or protein, including albumins and antibodies. In one embodiment of the invention, P is a PEG having an average molecular weight between 10,000 and 100,000, preferably between 20,000 and 60,000, and most preferably approximately 40,000. P may be linear, branched, or multi-arm. In some embodiments of the invention, P is a multi-arm PEG having 2-8 arms, each arm terminated with a functional group $Z^*$ (or Z). Examples of such multi-arm PEGs are those with $Z^*$ (or Z) groups at each end of a linear chain (2 arms) and those formed starting from pentaerythritol (4 arms), hexaglycerin (8 arms), tripentaerythritol (8 arms), or other similar branching cores.

pentaerythritol hexaglycerin

Tripentaerythritol

In a specific embodiment of the invention, P is a 4-armed PEG, L is a releasable linker of formula (2), D is somatostatin or its analog, and n=4. In a more specific embodiment of the invention, P is a 4-armed PEG, L is a releasable linker of formula (2) wherein m=0, $R^1$=CN or $R^3SO_2$, $R^2$=H, one $R^5$=H and the other $R^5$ is connected to P through functional groups Z and Z.

Figure 2:
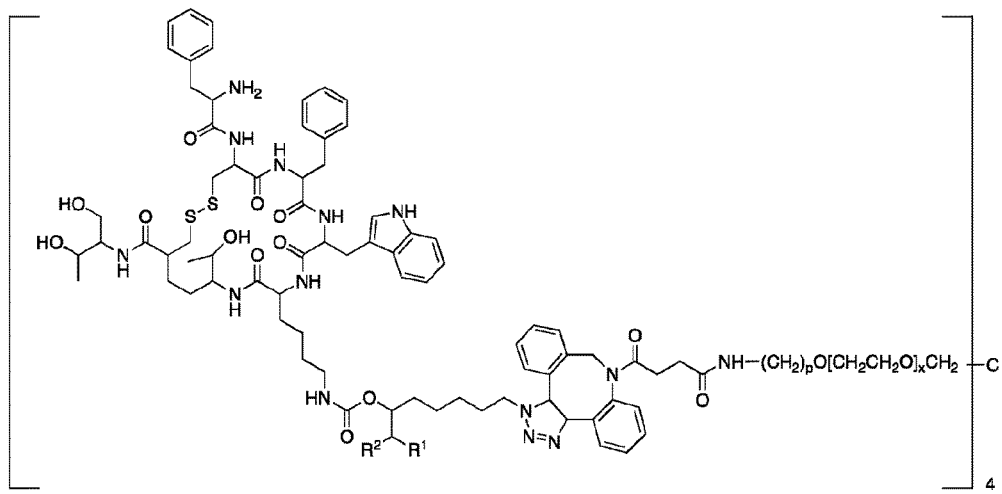
FIG. 2 illustrates a soluble conjugate of the invention wherein octreotide is releasably linked using a DBCO-derived triazole to a 4-arm PEG via the epsilon-amine.
Figure 3:
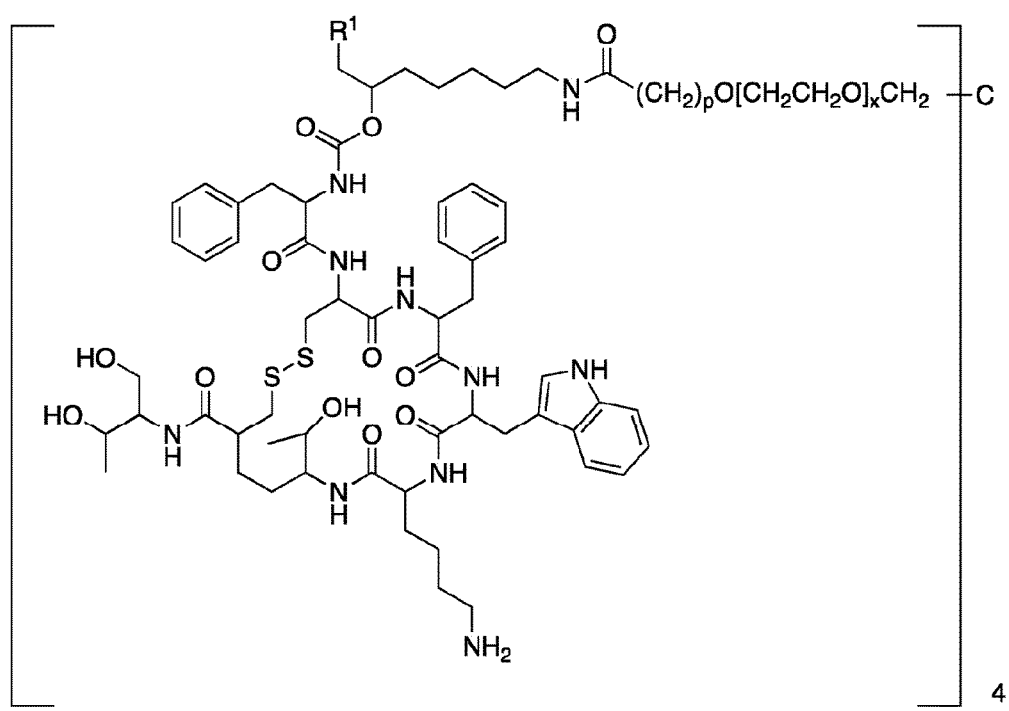
FIG. 3 illustrates a soluble conjugate of the invention wherein octreotide is releasably linked using an amide to a 4-arm PEG via the alpha-amine.
Figure 6:
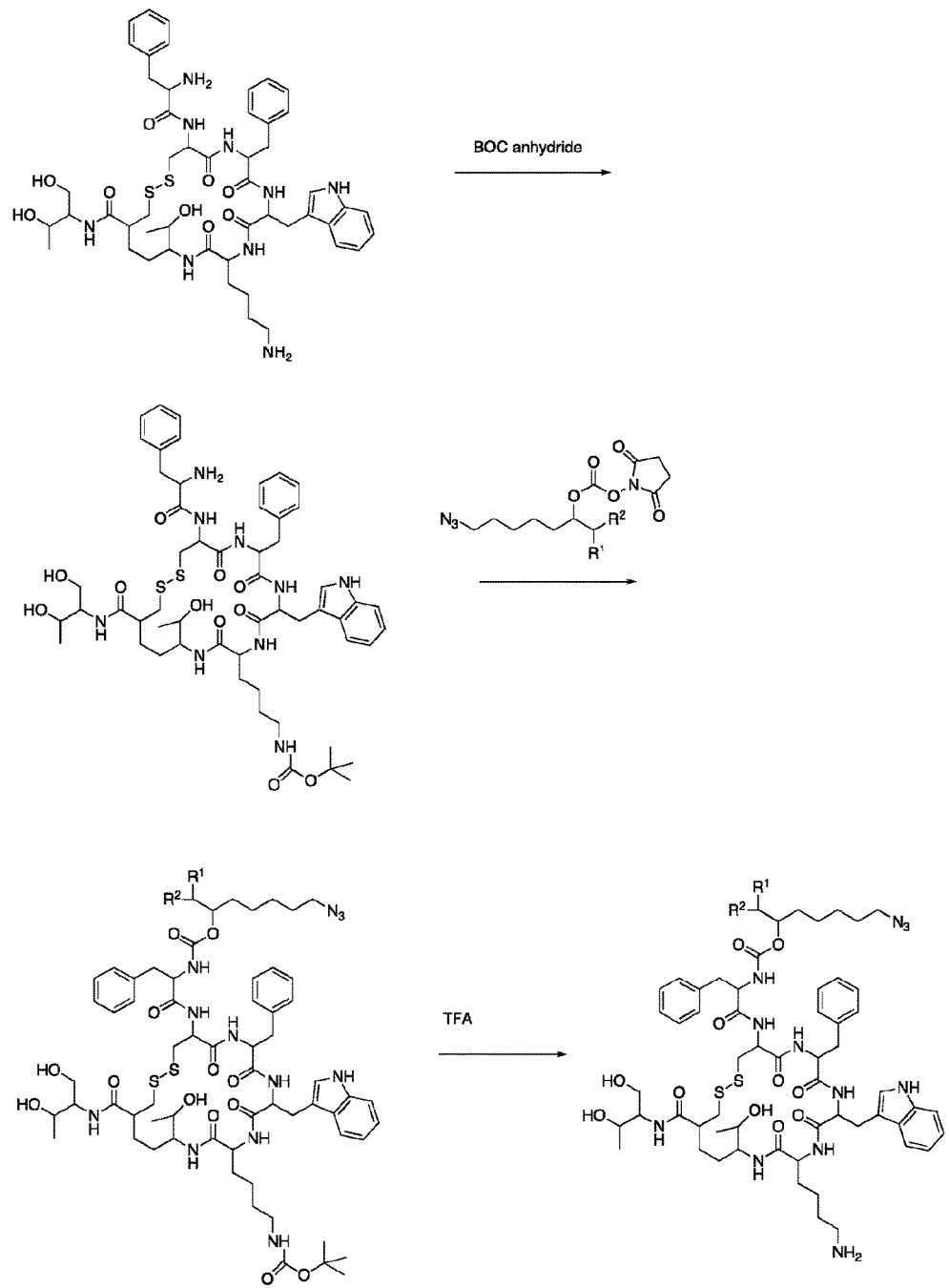
FIG. 6 illustrates a method for the preparation of alpha-linked azido-linker-octreotides.

Specific embodiments of the conjugates of formula (1) when P is a carrier molecule are illustrated in FIGS. 1, 2, and 3. FIG. 1 shows the structure of a conjugate wherein P is a 4-armed PEG connected to L via a triazole linkage formed by reaction of Z=azide and $Z^*$=cyclooctyne, and where L is connected to D via a carbamate to the $N_\alpha$-amino group of octreotide. The specific cyclooctyne used in this example is the dibenzoazacyclooctyne DBCO, but it is recognized that other cyclooctynes will work, including the bicyclononynes (BCN) and fluorinated cyclooctynes. To prepare such conjugates, a 4-armed PEG-tetraamine is derivatized with a cyclooctyne reagent, in this instance the active NHS ester of DBCO-succinic acid, to provide 4-armed PEG-(cyclooctyne)$_4$. Octreotide is mostly readily acylated at the $N_e$-amine of the lysine residue, and the linker can be attached to this position simply by treatment with an azido-linker-succinimidyl carbonate (PCT Publication WO2009/158668 A1; Santi et al., *Proc. Natl. Acad. Sci. USA* (2011) 109:6211-6216). To prepare azido-linker-octreotides linked via the alpha-amine, the lysine epsilon-amine group is first protected by reaction with an easily removable blocking group such as tert-butoxycarbonyl (BOC) (FIG. 6). The $N_e$—BOC-octreotide is then reacted with an azide-linker-OSu to acylate the remaining $N_a$-amino group, and the BOC is removed by treatment with acid. The resulting azido-linker-octreotide is then allowed to react with the PEG-(cyclooctyne)$_4$ to produce the conjugate of formula (1) wherein P=PEG, L=a releasable linker, D=octreotide linked via the $N_a$-amine, n=4, Z=azide, and Z*=cyclooctyne.

Figure 5:
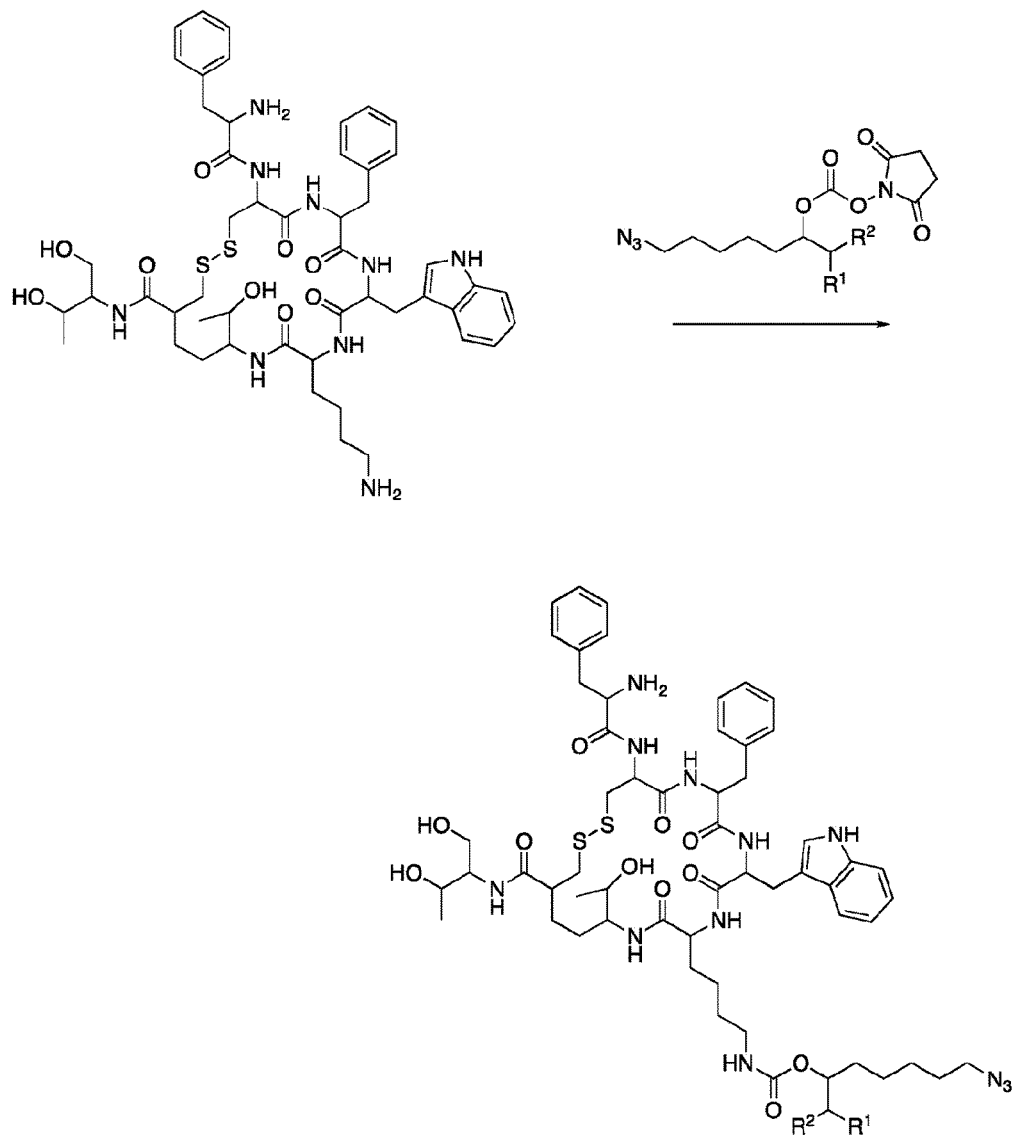
FIG. 5 illustrates a method for the preparation of epsilon-linked azido-linker-octreotides.

FIG. 2 shows the similar conjugate where L is connected to D via a carbamate to the $N_e$-amino group of octreotide. In this instance, octreotide is directly acylated with the azido-linker-OSu (FIG. 5), and the resulting $N_e$-linked azido-linker-octreotide is reacted with PEG-(cyclooctyne)$_4$ to produce the conjugate of formula (1) wherein P=PEG, L=a releasable linker, D=octreotide linked via the $N_e$-amine, n=4, Z=azide, and Z*=cyclooctyne.

Figure 4:
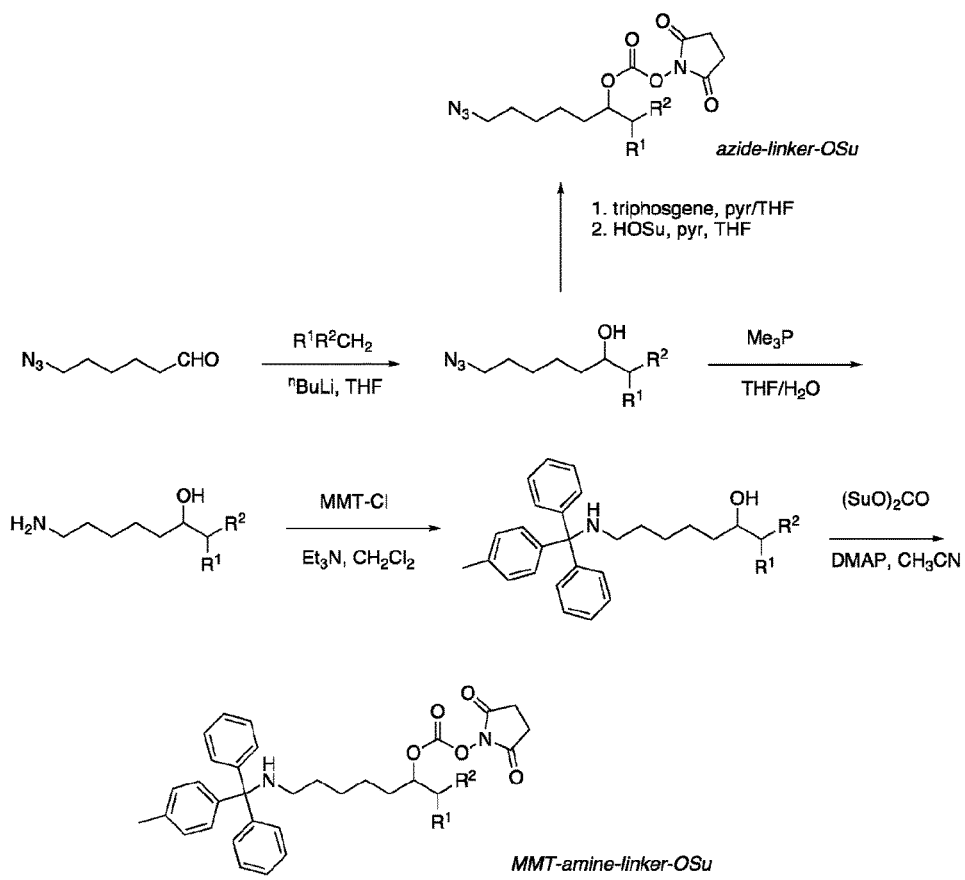
FIG. 4 illustrates method for the preparation of the linkers.
Figure 7:
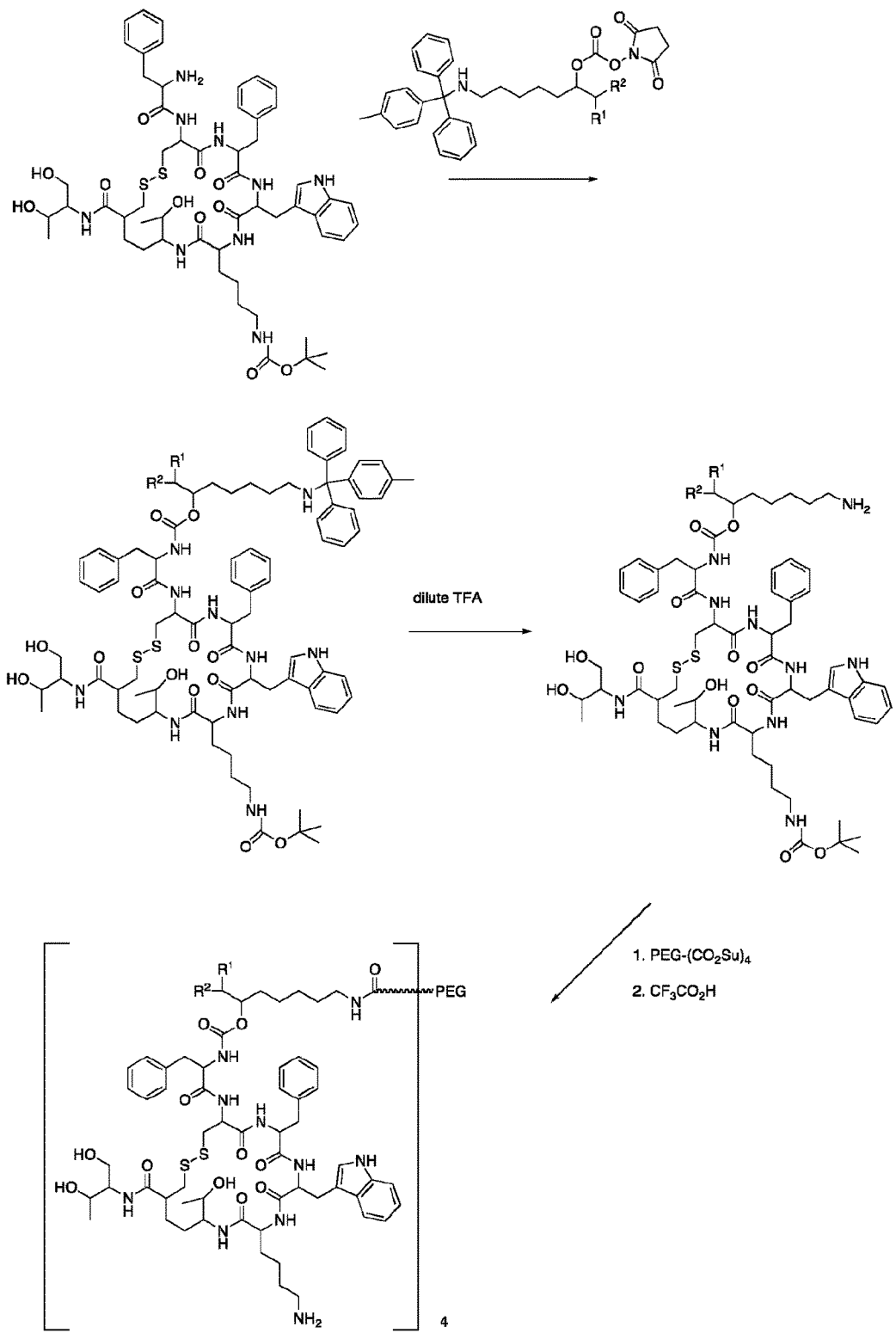
FIG. 7 illustrates a method for the preparation of a soluble conjugate of the invention wherein octreotide is releasably linked using an amide to a 4-arm PEG via the alpha-amine. In the Figure, PEG represents a multi-armed PEG.
Figure 8:
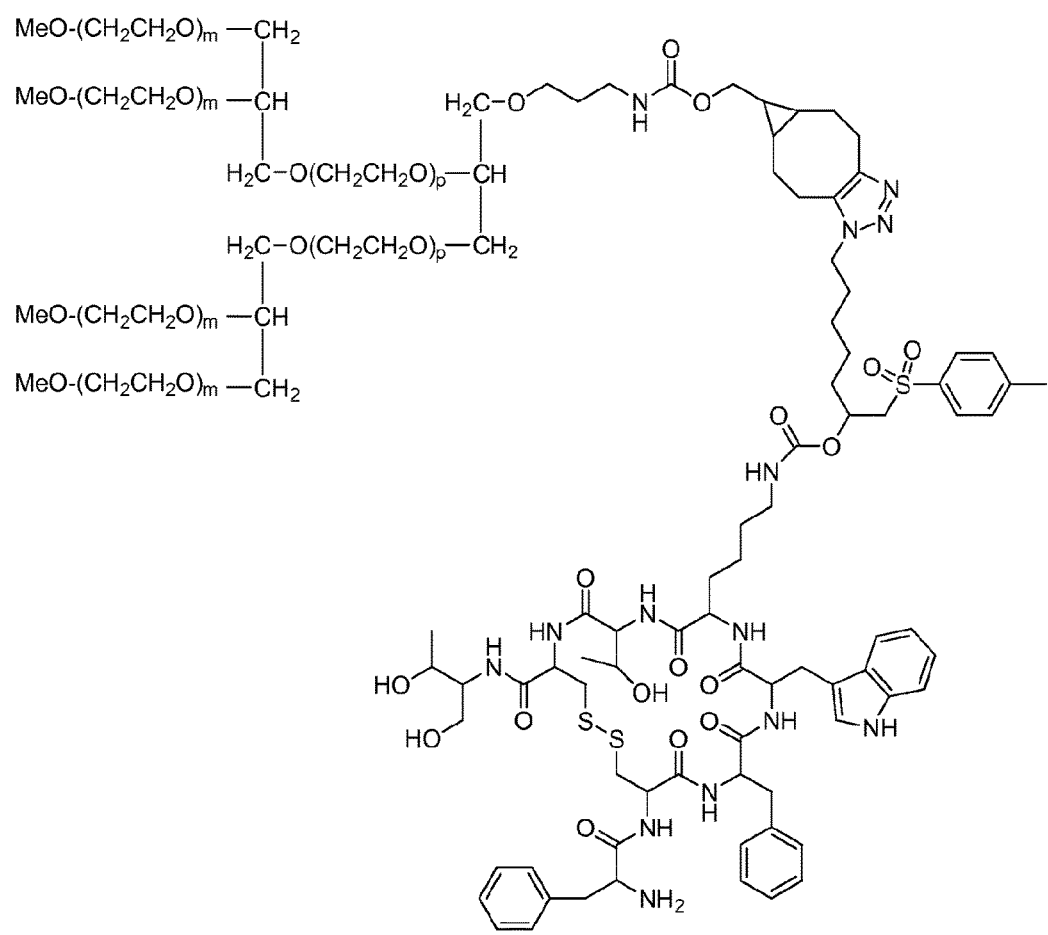
FIG. 8 shows the structure of a soluble octreotide conjugate of formula (1) wherein P is a 40-kDa 4-branched polyethylene glycol; L is a linker wherein R¹=(4-methylphenyl)SO₂, R² is H, one $R^5$ is H and the other is $(CH_2)_5Z$, wherein Z is a triazole formed by reaction of a BCN cyclooctyne with an azide; D=N-alpha-linked octreotide, and n=1. For the 40-kDa PEG, m is approximately 170 (7.5 kDa segments) and p is approximately 114 (5 kDa segments).

FIG. 3 shows the structure of a conjugate wherein P is a 4-armed PEG connected to L via an amide linkage formed by reaction of Z=amino and Z*=carboxylic active ester, and where L is connected to D via a carbamate to the $N_\alpha$-amino group of octreotide. This conjugate is prepared by reaction of a PEG-tetra(active ester), for example PEG-(succinimidyl succinate)$_4$ or PEG-(succinimidyl glutarate)$_4$, with an amino-linker-octreotide suitably protected on the non-conjugating amino group. The preparation of one such amino-linker-octreotide conjugate is illustrated in FIG. 7. The $N_e$—BOC-octreotide of FIG. 6 is reacted with a protected amino-linker wherein the protecting group is removable in the presence of the BOC group. One such suitable protecting group is monomethyltrityl (MMT), prepared as illustrated in FIG. 4. The MMT-linker-octreotide (BOC) is partially deprotected using mild acid, and the resulting amino-linker-octreotide is reacted with the PEG-(active ester)$_4$. A final deblocking with trifluoroacetic acid is then used to produce the final conjugate.

It will be recognized that similar conjugates can be prepared in analogous fashion by conjugation of other somatostatin analogs. Further, since most somatostatin analogs are synthetic peptides, the position of linker attachment can also be controlled by attachment during peptide synthesis.

In one embodiment of the invention, P is am insoluble hydrogel. The preparation of hydrogels having controllable drug release and degradation has been disclosed in PCT Publication WO2013/036847 A1. The above-described linker-somatostatin/analogs may further be attached to such hydrogels using chemistries analogous to those described above for soluble PEG conjugates.

The use of hydrogel conjugates of somatostatin/analogs may be favored over that of soluble conjugates in certain situations. For example, depending upon the location of conjugation, the somatostatin/analog may retain some degree of biological activity while conjugated. This may result in receptor-mediated endocytosis of the conjugate. Once inside the endosomal compartment, the conjugate may be degraded to release the carrier molecule; when the carrier molecule is PEG, it is stable to further degradation and is trapped in the endosomal compartment. This may lead to vacuole formation and associated toxicities. With non-circulating conjugates like hydrogels, this is not an issue.

To form hydrogels, a linker-somatostatin/analog such as those described above is allowed to react with a first macromonomer to form a drug-loaded macromonomer. This drug-loaded macromonomer is then allowed to react with a cross-linking macromonomer to form a cross-linked polymeric gel. Alternatively, the cross-linked polymeric gel may be formed first by reacting the two macromonomers, followed by attachment of the linker-somatostatin/analog, or all three components may be mixed and allowed to react simultaneously.

Figure 11:
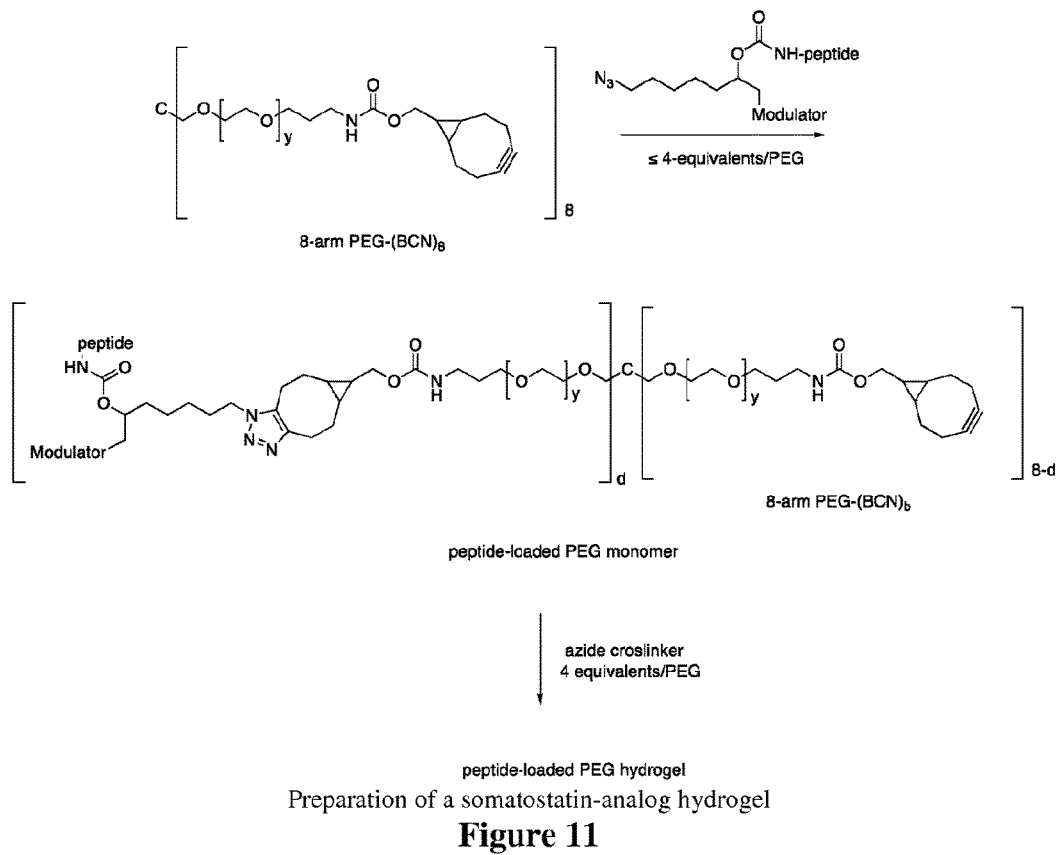
FIG. 11 illustrates a method for the preparation of hydrogels that release a somatostatin or analog peptide. In this method, an 8-armed PEG-(cyclooctyne)₈ macromonomer is reacted with ≤4 equivalents of azido-linker-peptide to connect up to 4 linker-peptides per 8-arm PEG macromonomer. The remaining cyclooctyne units are then used to form the hydrogel matrix by reaction with an azide-containing crosslinking reagent. In this figure, "C" represents a multi-armed core.

In one embodiment shown in FIG. 11, an 8-arm PEG-(cyclooctyne)$_8$ is allowed to react with q molar equivalents of azido-linker-D to produce an intermediate PEG-(linker-D)$_q$(cyclooctyne)$_{8-q}$, where q=the average number of attached linker-D per macromonomer. This drug-loaded macromonomer is then allowed to react with up to (8-q)/r molar equivalents of r-arm PEG-(linker-azide) to produce the hydrogel. Hydrogel formation requires at least 1.6 cross-links per macromonomer, and so q will be 0.01-6.4, preferably 0.1-6.0, and more preferably 0.1-4.0. Thus, in one embodiment of the invention, an 8-arm PEG-(cyclooctyne)$_8$ is allowed to react with q molar equivalents of azido-linker-D to produce an intermediate PEG-(linker-D)$_q$(cyclooctyne)$_{8-q}$. This drug-loaded macromonomer is then allowed to react with up to (8-q)/4 molar equivalents of 4-arm PEG-(linker-azide)$_4$ to produce the hydrogel. In a preferred embodiment of the invention, the drug-loaded macromonomer having q=0.1-4.0 is allowed to react with 1 molar equivalent of 4-arm PEG-(linker-azide)$_4$ to produce a hydrogel having on average 4 crosslinks per macromonomer.

In another embodiment of the invention, a 4-arm PEG is first derivatized with a molecule comprising two orthogonally-reactive functional groups Z and Y (i.e., selected from different columns but not members of the same pair in Table 1). This macromonomer is then conjugated to a Z*-linker-D through functional group Z as described above, and the second functional group Y is allowed to react with a second macromonomer comprising functional groups Y* that are complementary to Y. In this instance, up to 4 D molecules may be attached per first macromonomer, and a hydrogel having 4 crosslinks per macromonomer may be obtained.

As described in PCT Publication WO2013/036847 A1, the hydrogels may comprise further linkers that degrade by beta-elimination, thus providing control over the residence time of the hydrogels. The linker used to prepare the hydrogel matrix preferably has beta-elimination rate from 2 to 10-times slower than the linker used to link the somatostatin or its analog to the hydrogel, more preferably from 3 to 6-times slower.

Pharmaceutical formulations of the soluble conjugates of the invention may be formulated using pharmaceutically acceptable excipients known in the pharmaceutical arts. In one embodiment of the invention, the pharmaceutical formulation comprises a soluble conjugate of the invention and an aqueous buffer at a pH value between 4 and 8, preferably between 4 and 7, and most preferably about pH 5. The formulation may optionally be lyophilized to provide a powder which may then be reconstituted with sterile water for injection prior to use.

Hydrogels of the invention may be prepared as microspheres or similar suspended particles suitable for injection, or the macromonomers may be provided as solutions or powders for reconstitution that, when mixed in the appropriate ratios immediately prior to use, may be injected as a liquid that subsequently forms a solid hydrogel in the desired compartment. Mixing may occur via a multi-barrel syringe fitted with a mixing tip.

Administration and Use

The conjugates of the invention and compositions thereof are useful for the same indications for which somatostatin and its analogs are currently indicated, including hydrogels comprising these analogs prepared according to the invention.

The Food and Drug Administration (FDA) has approved the usage of a salt form of this peptide, octreotide acetate, as an injectable depot formulation for the treatment of growth hormone producing tumors (acromegaly and gigantism), pituitary tumors that secrete thyroid stimulating hormone (thyrotropinoma), diarrhea and flushing episodes associated with carcinoid syndrome, and diarrhea in patients with vasoactive intestinal peptide-secreting tumors (VIPomas).

Dosage levels and modes of administration are dependent on the nature of the conjugate or hydrogel and the rate of release as well as the condition and the parameters associated with the patient. Such dosages and modes are within the judgment of the practitioner. The compositions of the invention may thus be administered by injection or, if properly formulated, orally, topically or by suppository, etc.

The following examples are intended to illustrate and not limit the invention. All references cited herein are hereby incorporated by reference in their entireties unless otherwise indicated.

Example 1

MMT-Amino Linker Alcohol

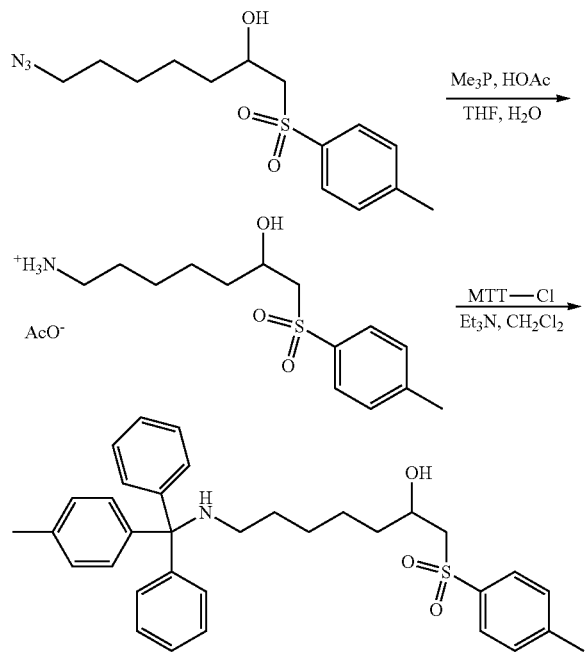

A solution of 1.0 M trimethylphosphine in THF (2.1 mL, 2.1 mmol) was added to a solution of 7-azido-1-(4-methylphenylsulfonyl)-2-heptanol (311 mg, 1.0 mmol) and acetic acid (0.135 mL, 2.4 mmol) in 1.0 mL of THF. Gas evolved, and after 50 min water (0.05 mL, 2.8 mmol) was added. After an additional 30 min, the mixture was evaporated to dryness, and the residue was triturated with 2×10 mL of ether. The residue was mixed with 5 mL of ethyl acetate and 2 mL of 1 N HCl, and the aqueous phase was collected and evaporated after addition of 5 mL of ethanol. The resulting crude amine acetate salt was dissolved in 5 mL of $CH_2Cl_2$, and triethylamine (0.5 mL, 3.6 mmol) and monomethyltrityl chloride (450 mg, 1.5 mmol) were added. After 15 min, the mix was diluted into $CH_2Cl_2$ and washed twice with 0.1 M $KP_i$, pH 6.0, followed by brine, dried over $mgSO_4$, filtered, and evaporated. The crude product was chromatographed in $SiO_2$ using a step gradient from 0-50% ethyl acetate/hexane to provide the product as a colorless oil (318 mg, 0.6 mmol, 60%). $^1$H-NMR ($CDCl_3$, 400 MHz): δ 7.80 (2H, d, J=8 Hz), 7.45 (4H, m), 7.37 (2H, d, J=8 Hz), 7.33 (2H, d, J=8 Hz), 7.25 (4H, m), 7.16 (2H, m), 7.07 (2H, d, J=8 Hz), 4.12 (1H, m), 3.72 (1H, br s), 3.18 (1H, dd, J=9, 14 Hz), 3.12 (1H, dd, J=2, 14 Hz), 2.45 (3H, s), 2.30 (3H, s), 2.08 (2H, t, J=7 Hz), 1.7-1.5 (8H, m).

Example 2

MMT-Amino Linker Succinimidyl Carbonate

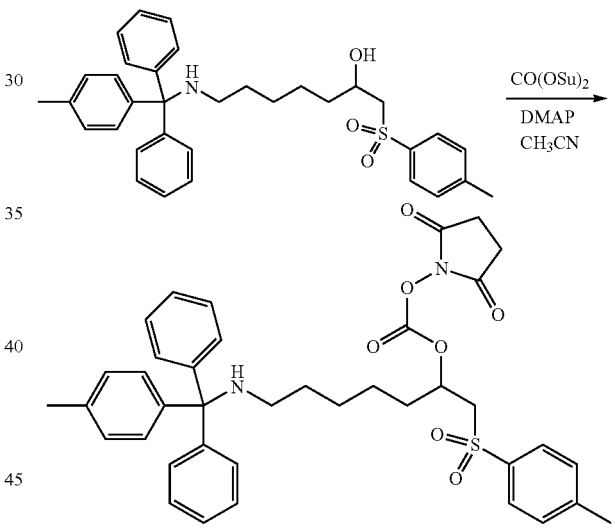

A suspension of the MMT-amino linker alcohol of Example 1 (180 mg, 0.33 mmol), disuccinimidyl carbonate (425 mg, 1.66 mmol), and 4-(dimethylamino)pyridine (84 mg, 0.69 mmol) in 2 mL of dry acetonitrile was stirred for 16 h. The resulting clear solution was diluted into ethyl acetate and washed with water followed by brine, then dried over $mgSO_4$, filtered, and evaporated. The product was purified by $SiO_2$ chromatography using a step gradient of ethyl acetate in hexane to provide 190 mg (84%) of a colorless glass.

Example 3

Preparation of N-Alpha-Linked Azido-Linker-Octreotide

Preparation of Octreotide(Boc).

Octreotide (10.2 mg, 10 umoles, 20 mM final concentration) and di-(tert-butyl) dicarbonate (9.1 umoles, 18.2 mM final concentration) were combined in 500 uL DMF. After 4 hours the reaction was purified by semi-prep HPLC on a Hi-Q 5u C18 column (50×20 mm ID, Peek scientific) with a gradient of 20% ACN 0.1% TFA to 100% ACN 0.1% TFA over 15 min at a 5 mL/min flow rate. Each 500 uL fraction was neutralized by addition of 15 uL of saturated $NaHCO_3$ and dried under vacuum.

Preparation of N-Alpha-Linked Azido-Linker-Octreotide.

Octreotide(Boc) (360 nmoles, 3.6 mM final concentration) and 7-azido-1-(4-methylphenylsulfonyl)-2-heptyl succinimidyl carbonate (1.1 umoles, 11 mM final concentration) were combined in 0.1 mL DMF. After 5 hours the reaction was complete by HPLC (peak shift from 7.3 minutes to 9.3 minutes) and was purified by HPLC as above. Purified fractions were dried under vacuum and brought up in 200 uL of 50% TFA in dichloromethane to remove the Boc protecting group. To the purified product, 1 mL of 50% TFA/dichloromethane was added. After 1 hr the reaction was analyzed for completion by HPLC. DCM/TFA was removed under vacuum. The product N3-($\alpha$-amine) octreotide was verified by MSMS.

Example 4

Preparation of N-Epsilon-Linked Azido-Linker-Octreotide

Octreotide (6.7 umoles, 22 mM final concentration) and 7-azido-1-(4-methylphenylsulfonyl)-2-heptyl succinimidyl carbonate (8 umoles, 26.4 mM final concentration) were combined in 0.3 mL DMF. After 3 hours the reaction was purified by semi-prep HPLC on a Hi-Q 5u C18 column (50×20 mm ID, Peek scientific) with a gradient of 20% ACN 0.1% TFA to 100% ACN 0.1% TFA over 15 min at a 5 mL/min flow rate. Fractions were dried under vacuum and identified by MS and MSMS analysis. Acylation of octreotide in DMF resulted in formation of the monoacyl ($\epsilon$-amine) octreotide (~91% by HPLC peak area 280 nm) and bisacyl octreotide (9%) as identified by MS and MSMS analysis. Purification by C18 column gave a 75% final yield of the monoacyl ($\epsilon$-amine) octreotide with no noticeable contamination by HPLC.

Example 5

Preparation of Soluble PEG-Linker-Octreotide

Preparation of 4-arm $PEG_{40\ kDa}$-$(BCN)_4$.

4-arm $PEG_{40\ kDa}$ amine (NOF PTE400PA) (100 mg, 2.5 umole) was combined with BCN—OPNP (SynAffix, 4 mg, 12.5 umole) in 1 mL of DMF containing N,N-diisopropylethylamine (28.8 umole). After 2 hours at room temperature, the reaction was diluted to 2.5 mL with $H_2O$ and dialyzed against 1 L of $H_2O$ with a 12 kDa dialysis membrane. Dialysis buffer was changed after 4 hours and left overnight. The dialysis buffer was changed to 1 L of MeOH and replaced after 4 hours. The product was dried by evaporation and dissolved in 1.5 mL THF. The product was precipitated by dropwise addition to 15 mL methyl tert butyl ether with stirring. After 30 minutes, the precipitate was pelleted by centrifugation, decanted and washed twice with 3 mL MTBE. The resulting powder was dried under vacuum. TNBS assay was performed to quantify any remaining free amines.

Preparation of Conjugate.

N-epsilon-linked azide-linker-Octreotide from Example 4 (4.4 umoles, 0.7 mM final concentration) was combined with 4-arm $PEG_{40\ kDa}$-$BCN_4$ (4 umole BCN, 0.64 mM final concentration) in 600 µL DMF. The reaction progress (consumption of octreotide) was followed by HPLC on a size exclusion column (BioSep™ SEC 2000 300×7.8 mm HPLC column (Phenomenex)) with an isocratic flow of 50% ACN/$H_2O$ 0.01% TFA at 1 mL min$^{-1}$ using a Shimadzu™ Prominence HPLC with a diode array detector. After 19 hours the reaction was diluted with 5 mL of 10 mM triethanolamine pH 7.0. In 2 equivalent volumes, the reaction was purified over a 1 mL HiTrap SP FF ion exchange column (Phenomenex®) equilibrated with 10 mM NaOAc pH 5.0 (pI~9). The column was washed with 6 mL 10 mM NaOAc pH 5.0 (buffer) followed by 6 mL buffer containing 50 mM NaCl, 100 mM NaCl, 150 mM NaCl, and 500 mM NaCl. The absorbance spectrum of each elution fraction was measured and fractions containing peptide absorbance were analyzed by HPLC SEC for identity (see above). The flow through and buffer wash fractions were combined and concentrated to ~500 µL by centrifugation using a 10 kDa MWCO spin concentrator (Millipore) followed by dilution to 5 mL with 10 mM NaOAc pH 5.0. Concentration/dilution was repeated 4× to complete buffer exchange. The product is shown schematically in FIG. 2.

A stable (i.e., non-releasable) conjugate where $R^1R^2CH$ is absent was prepared similarly for use as a control in the release kinetics experiments.

Example 6

Figure 9:
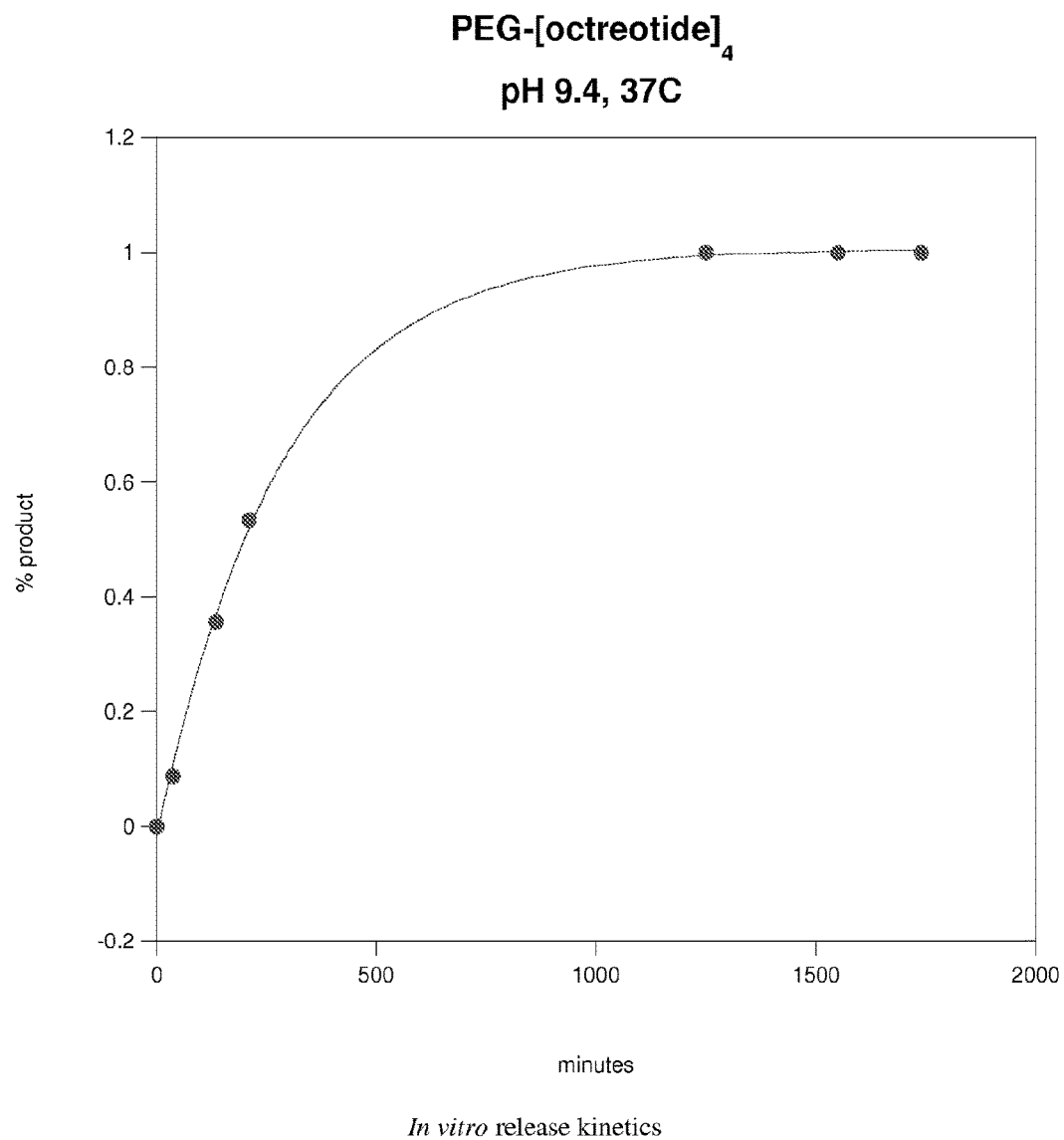
FIG. 9 shows the kinetics of in vitro release of octreotide from the conjugate of FIG. 8 at pH 9.4, 37° C. Octreotide is released from the conjugate with a first-order half-life of 4 hours, corresponding to a half-life of 400 hours at pH 7.4.

Elimination Kinetics of 4-Arm $PEG_{40\ kDa}$ ($\epsilon$-Linked) MePhSO2 Octreotide The kinetic assay containing 20 µM 4-arm $PEG_{40\ kDa}$ ($\epsilon$-linked) octreotide conjugate of Example 5 ($R^1$=4-methylphenyl-$SO_2$) in 100 mM buffer (Na Borate, pH 9.4) containing 50 uM azido-PEG-DNP internal standard was incubated at 37° C. At intervals over five half-lives, 25 µL aliquots were removed, quenched with 5 µL of 4M HOAc and stored at −20° until analysis. Samples were analyzed on a Jupiter 5µ C18 300A 150×4.6 mm HPLC column (Phenomenex®) using a linear gradient of 20-100% ACN-0.1% TFA at 1 mL min$^{-1}$ on a Shimadzu™ Prominence HPLC with a photo diode array detector. Release rates ($k_{obsd}$) were calculated by fitting the % reaction vs time to the first-order rate equation. Measurement of the elimination $t_{1/2}$ of the conjugate at pH 9.4 37° C. was 4 hrs (extrapolating to 400 hr at pH 7.4 37° C.). See FIG. 9.

Example 7

In Vivo Pharmacokinetics

PK assays on the conjugates of Example 5 were performed on cannulated Sprague Dawley rats. IV injections were made at 1 mL/kg body weight with stable conjugate at 348 µM (13.9 mg/kg conj, 0.35 mg/kg octreotide) or 2 mL/kg body weight with the releasable conjugate (Example 6) at 697 µM (56 mg/kg conj., 1.4 mg/kg octreotide) in 10 mM NaOAc at pH 5.0. Blood samples were collected at 0, 1, 2, 4, 8, 12, 24, 48, 72, and 120 hours. At each timepoint a 300 µL blood sample was added to 30 µL of a 1M citrate/0.1% Pluronic® F68 solution, pH 4.5 to lower the pH and remove coagulation factors to give plasma.

A portion of the plasma samples were precipitated by addition of 3 parts acetonitrile and centrifuged at 16000×g for 10 minutes. The samples were analyzed by HPLC for PEG-peptide conjugate and PEG-remnant concentrations. Concentrations were calculated by comparison of peak areas to a standard curve.

Figure 10:
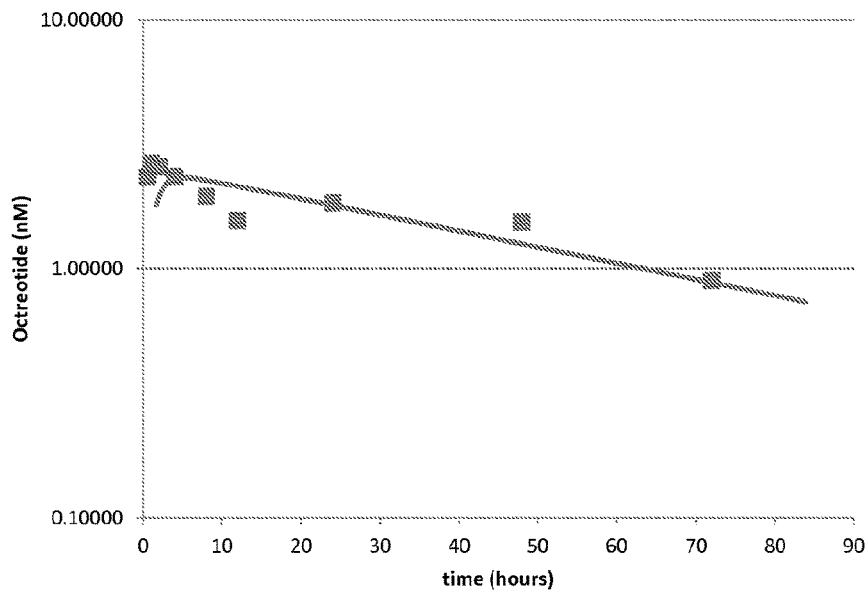
FIG. 10 shows the pharmacokinetics of octreotide released from the conjugate of FIG. 8 after i.v. administration to rats.

A portion of the releasable plasma samples was analyzed by LC/MSMS for free octreotide (MedPace). The plasma sample concentration vs time data for the free octreotide is shown in FIG. 10.

When analyzed individually using PK solutions software, the stable conjugate was calculated to have a t½ of 35 hr, in line with previous measurements of stable PEG-peptide conjugates of ~40 hr. The volume of distribution (100 mL/kg) is also in line with previous PEG conjugate, typically measured at the approximate blood volume of the rat (70 mL/kg). The free octreotide had a calculated elimination t½ of 50 hours.

Example 8

Preparation of Triazole-Coupled Octreotide Hydrogels

A 200 mg/mL (40 mM cyclooctyne) solution of 40-kDa eight-armed PEG-(BCN)$_8$ (ref to hydrogel paper) in DMF (250 uL, 10 umol cyclooctyne) was mixed with a 53.2 mM solution of epsilon-linked azido-linker-octreotide (modulator=CH$_3$SO$_2$) in DMF (75.2 uL, 4.0 umol azide) and 5 uL of 30 mM azido-fluorescein in methanol (0.15 umol azide) and allowed to stand for 1 h at 37° C. DMF (544.8 uL) was added, followed by a 200 mg/mL (40 mM azide) solution of 20-kDa 4-armed PEG-(NH(CO)—O—CH(CH$_2$SO$_2$NEt$_2$)(CH$_2$)$_5$N$_3$ in DMF (125 uL, 5 umol azide). The gel mixture was quickly pipetted into 16 circular rubber gel molds (9 mm dia×1 mm depth) on silanized glass slides, with 60 uL per mold, and allowed to set for 1 h. The gels were then removed from the molds and washed 1×10 mL of water for 1 h, 1x 10 mL of 100 mM acetate buffer, pH 5.0, for 1 h, and finally 1×10 mL of 10 mM acetate, pH 5.0, 0.1% sodium azide at 4° C. overnight. Gels were sterilized by soaking in 10 mL of 70% ethanol for 24 h, then were washed 3×10 mL of sterile-filtered water.

Gels comprising epsilon-linked azido-linker-octreotide (modulator=(4-methyl-phenyl)-SO$_2$ were similarly prepared by adjusting the volumes of added peptide (84.4 mM in DMF; 47.4 uL, 4.0 umol azide) and DMF (572.6 uL) to account for concentration differences in the azido-linker-octreotide stocks.

Gels comprising alpha-linked azido-linker-octreotide (modulator=(4-methyl-phenyl)-SO$_2$ were similarly prepared by mixing 200 mg/mL 40-kDa PEG-(BCN)$_8$ (62.5 uL, 2.5 umol cyclooctyne) and the alpha-linked azido-linker-octreotide (modulator=4-(methylphenyl)SO$_2$; 30 uL, 0.91 umol azide), standing for 30 min at 37° C., then adding DMF (126.2 uL) and 200 mg/mL 20-kDa PEG(-NH(CO)—O—(CH$_2$)$_6$N$_3$ in DMF (31.3 uL, 1.25 umol azide) and pipetting 60 uL of the gel mixture into each of four 9×1 mm circular rubber molds. After standing overnight, the gels were washed as described above.

The products are shown schematically in FIG. 11.

Example 9

Preparation of Hydrogel Macromonomers with Differentiated Functional Groups

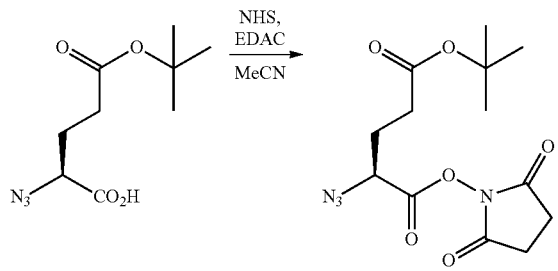 [SMILES: "MeCN" ; CC(C)(C)OC(=O)CC[C@H](N=[N+]=[N-])C(=O)O ; CC(C)(C)OC(=O)CC[C@H](N=[N+]=[N-])C(=O)ON1C(=O)CCC1=O]

N$_3$-Glu(OtBu)-OSu.

(S)-2-Azido-glutaric acid 5-tert-butyl ester (dicyclohexylammonium) salt (195 mg, 474 µmol) was dissolved in 20 mL of ethyl acetate then washed successively with 6% phosphoric acid (2×10 mL), water (2×10 mL), and brine (10 mL). The organic layer was dried over mgSO$_4$, filtered, and concentrated by rotary evaporation to provide (S)-2-azido-glutaric acid 5-tert-butyl ester (100 mg, 435 µmol). The resultant colorless oil was used without further purification. N-Hydroxysuccinimide (75 mg, 0.65 mmol) and EDAC (125 mg, 0.651 mmol) were successively added to a solution of (S)-2-azido-glutaric acid 5-tert-butyl ester (100 mg, 435 µmol) in 2 mL of acetonitrile. The reaction mixture was stirred at ambient temperature overnight then partitioned between 40 mL of 1:1 ethyl acetate:KHSO$_4$ (5% aq). The layers were separated, and the organic phase was successively washed with water, NaHCO$_3$ (sat aq), water, and brine (1×20 mL each). The organic layer was then dried over mgSO$_4$, filtered, and concentrated. The crude concentrate was purified by silica gel column chromatography (pipette column) eluting with dichloromethane:hexanes (3:7 then 7:3, 3 mL each) followed by 3 mL of dichloromethane and finally acetone:dichloromethane (1:3). Hydrolysis was observed during the silica gel chromatography step (~10 min). Product-containing fractions were combined and diluted with 5 mL of dichloromethane. Hydrolysis byproducts were removed by successively washing the dichloromethane solution with NaHCO$_3$ (sat aq), water, and brine (1×3 mL each). The organic layer was then dried over mgSO$_4$, filtered, and concentrated to provide 34 mg (24%) of the title compound as a tan oil.

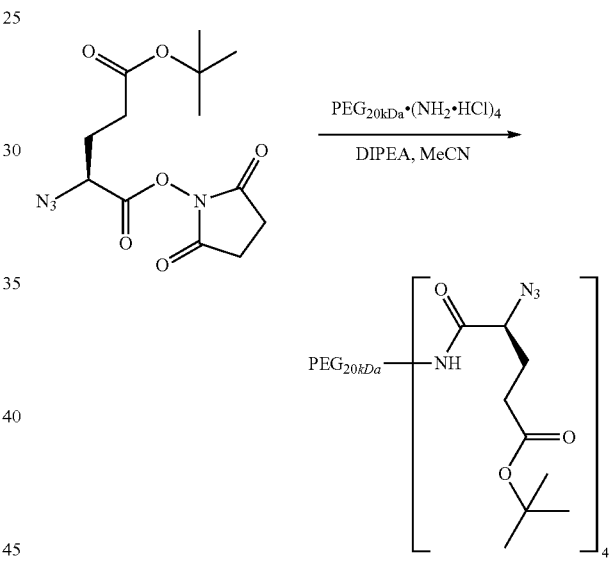

[N$_3$-Glu(OtBu)]$_4$-PEG$_{20\ kDa}$.

A solution of N$_3$-Glu(OtBu)-OSu (20 mg, 61 µmol) in 0.5 mL of acetonitrile was added to a stirred solution of 20 kDa PEG amine.HCl (275 mg, 13.8 µmol PEG, 55.0 µmol amine) and N,N-diisopropylethylamine (21 µL, 0.12 mmol) in 2.75 mL of acetonitrile. After stirring for 1.5 h at ambient temperature, TNBS assay (LOQ=0.5%) indicated that 0.8% of the initial free amine remained in the reaction mixture. N,N-Diisopropylethylamine (21 µL, 0.12 mmol) and acetic anhydride (5.2 µL, 55 µmol) were then added to cap any unreacted amine. The reaction mixture was stirred at ambient temperature for 30 min more then concentrated to ~1 mL. The product was precipitated by dropwise addition to 15 mL of vigorously stirred tert-butyl methyl ether. The reaction vial was washed with 0.3 mL of acetonitrile, and the wash was added to the precipitation mixture. After stirring for 30 min, the mixture was vacuum filtered. The solid product was triturated with tert-butyl methyl ether (3×5 mL) then dissolved in 3 mL of acetonitrile and dialyzed (12-1400 MWCO) against 600 mL of acetonitrile for 60 h. The retentate was concentrated to provide 238 mg (83%) of the title compound as a white film.

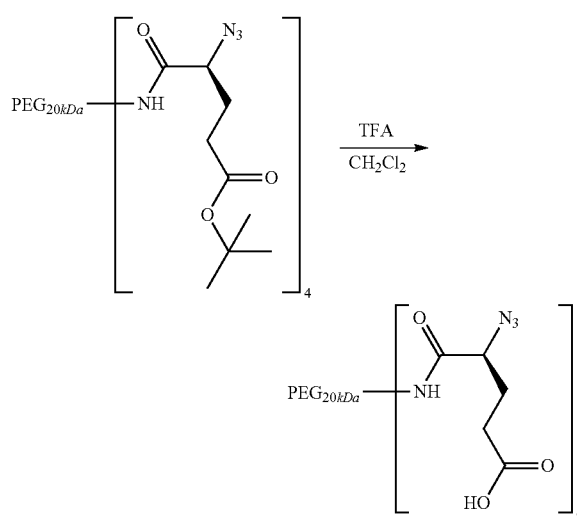

[N$_3$-Glu]$_4$-PEG$_{20\,kDa}$.

Trifluoroacetic acid (2.4 mL) was added to a solution of [N$_3$-Glu(OtBu)]$_4$-PEG$_{20\,kDa}$ (238 mg, 11.4 µmol) in 2.4 mL of dichloromethane. After stirring at ambient temperature for 3.5 h, the reaction was complete as judged by HPLC analysis. The reaction mixture was concentrated to dryness, and the resulting oil was triturated with tert-butyl methyl ether (15 mL) until a white precipitate formed. The suspension was vacuum filtered. The solid was washed with tert-butyl methyl ether (3×5 mL) then dried under vacuum to provide 211 mg (89%) of the title compound as a white powder.

Figure 12:
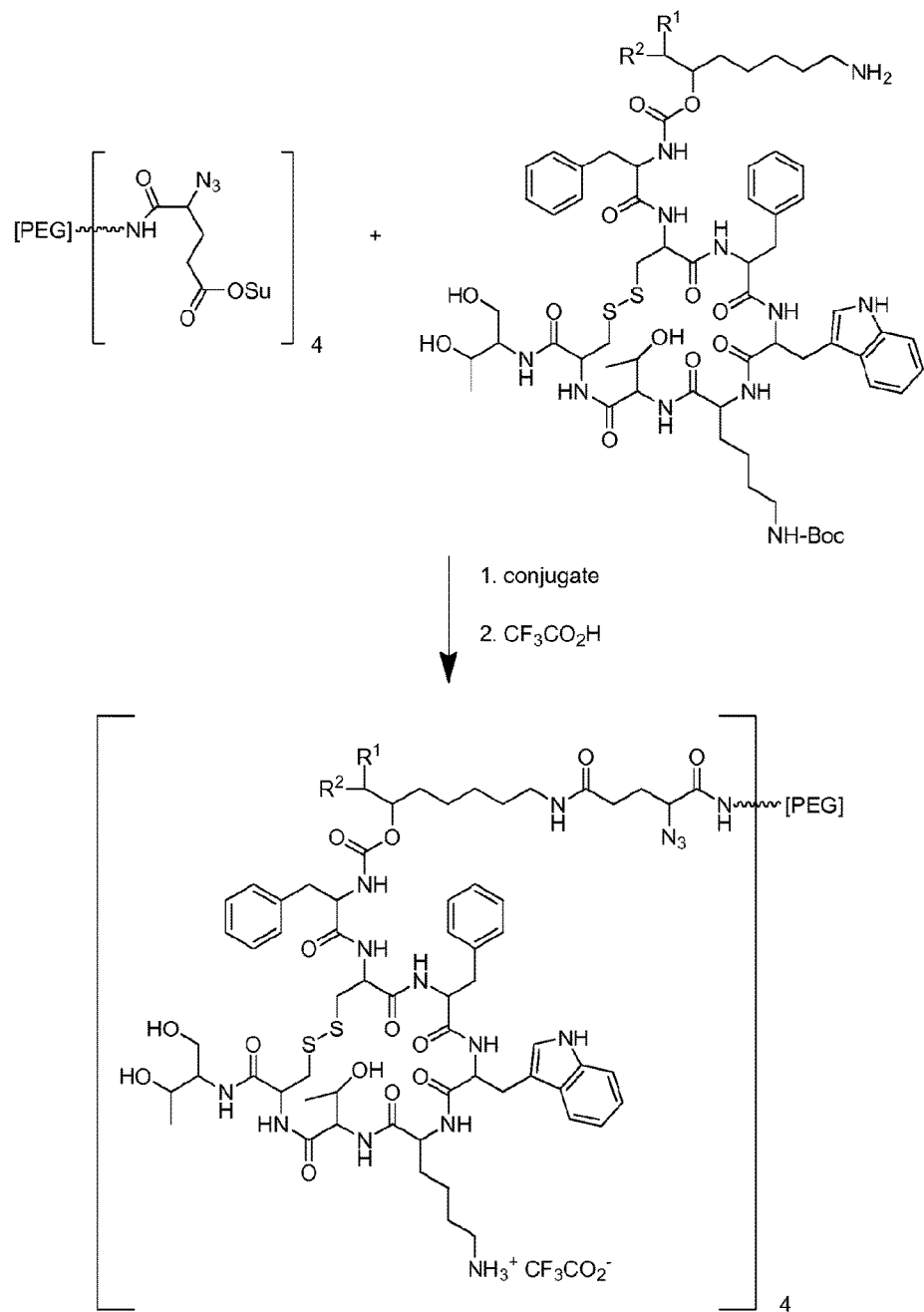
FIG. 12 illustrates the first step in a second method for the preparation of hydrogels that release a somatostatin or analog peptide. In this method, a four-armed PEG macromonomer comprising two orthogonally-reactive functional groups on each arm is reacted with a linker-peptide wherein the linker comprises a functional group that reacts with one of the two macromonomer functional groups. The resulting peptide-loaded macromonomer is then reacted with a crosslinking reagent having functional groups reactive with the remaining functional group on the PEG macromonomer. In the first step illustrated, the PEG-macromonomer comprises a succinimidyl ester for connecting to an amino-linker-somatostatin/analog and an azide for subsequent crosslinking with a second macromonomer comprising a cyclooctyne. In this Figure, PEG is multi-armed.
Figure 13:
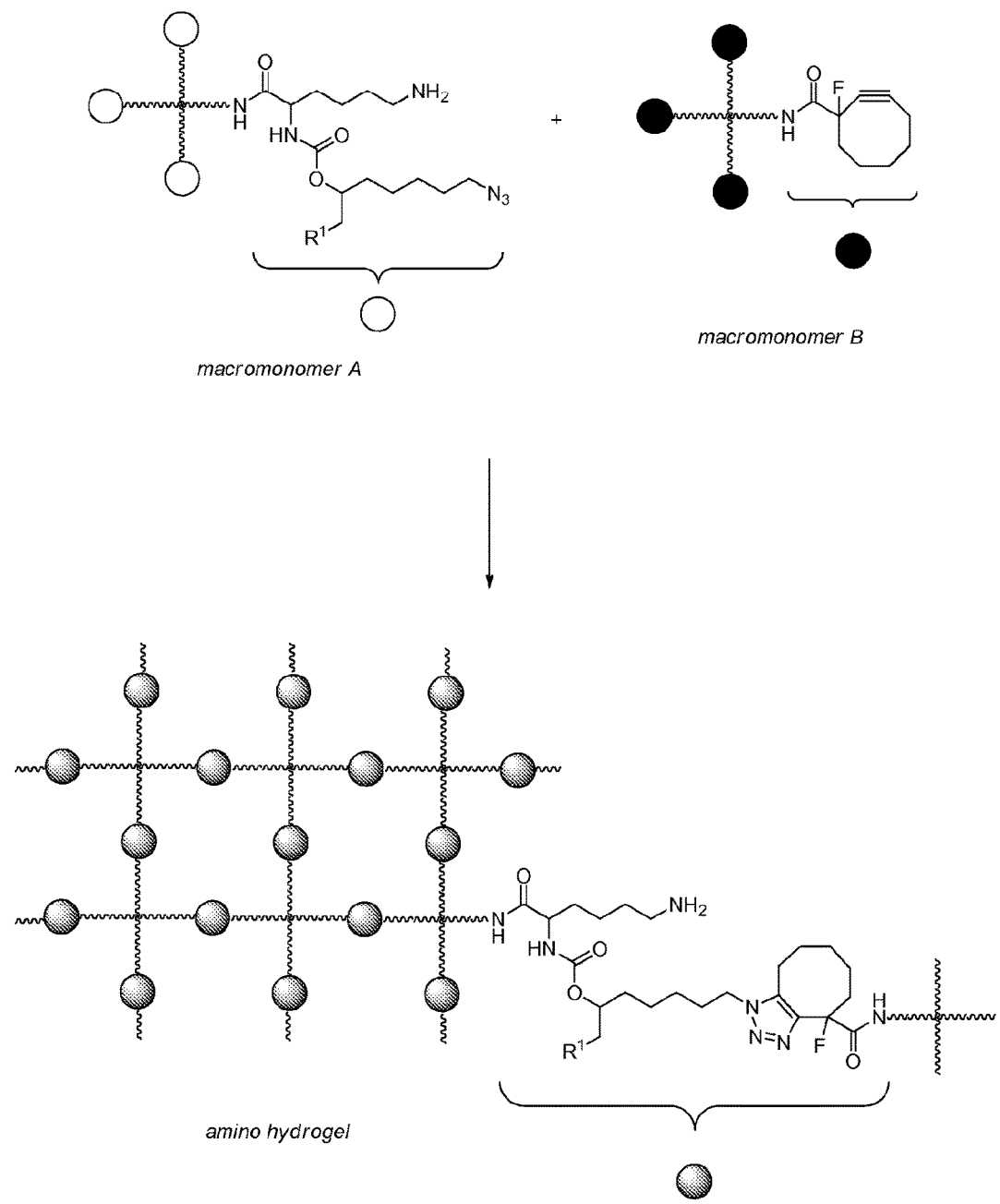
FIG. 13 shows the formation of a hydrogel by coupling a drug-bearing macromonomer with an azido functional group to a crosslinking macromonomer with a cyclooctyne functional group.
Figure 14:
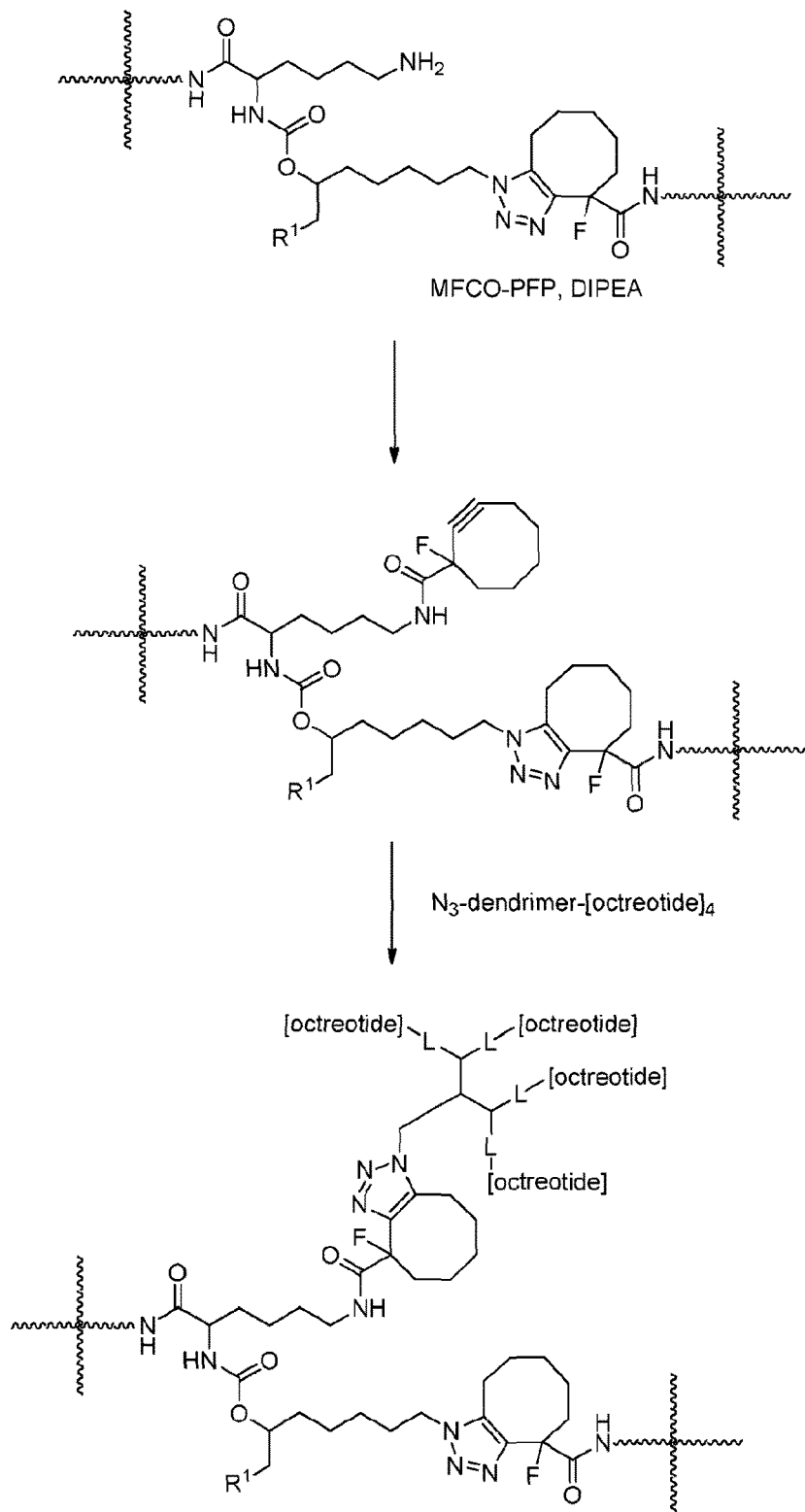
FIG. 14 shows loading of the resulting hydrogel with an azido-coupled dendrimer containing the somatostatin or its analog.

The resulting product is designated "Conjugate" in FIG. 12.

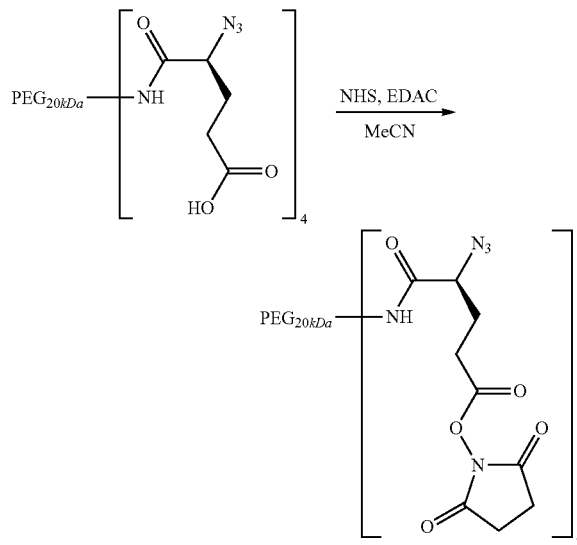

[N$_3$-Glu(OSu)]$_4$-PEG$_{20\,kDa}$.

N-Hydroxysuccinimide (9.2 mg, 80 µmop and EDAC (15 mg, 78 µmol) were successively added to a solution of [N$_3$-Glu]$_4$-PEG$_{20\,kDa}$ (211 mg, 10.2 µmol) in 2.5 mL of acetonitrile. The reaction mixture was stirred at ambient temperature overnight then more N-hydroxysuccinimide (9.2 mg, 80 µmol) and EDAC (15 mg, 78 µmol) were added. After again stirring at ambient temperature overnight (44 h total), the reaction mixture was dialyzed (12-14000 MWCO) against acetonitrile (800 mL, 18 h; then 500 mL, 24 h). The retentate was concentrated to ~1.5 mL, and the product was precipitated by addition to vigorously stirred tert-butyl methyl ether (17 mL). The mixture was stirred at ambient temperature for 1 h then vacuum filtered. The solid was washed with tert-butyl methyl ether (3×3 mL) then dried under vacuum to provide 154 mg (72%) of the title compound as a white powder. The resultant product is shown in FIG. 12.

Example 10

Preparation of Amino-Linker-Octreotide(Boc)

Preparation of N-Alpha-Linked MTT-Amino-Linker-Octreotide.

Solutions of octreotide(Boc) (28.5 mM in DMSO; 350 uL, 10 umoles) and 7-(monomethyl-tritylamino)-1-(4-methylphenylsulfonyl)-2-heptyl succinimidyl carbonate (140 mM in THF; 140 uL, 19.6 umoles) were combined. After 16 hours the reaction was complete by HPLC (peak shift from 7.1 minutes to 9.5 minutes) and was purified by HPLC as above. Purified fractions were combined, neutralized with sodium bicarbonate, and dried under vacuum to provide the amino-linker-octreotide(Boc) where the modulator group R$^1$ is 4-methylphenylsulfonyl. MS showed the expected [M+H]$^+$=1687.2. Similarly prepared were amino-linker-octreotide(Boc) where the modulator group R$^1$ is CN ([M+H]$^+$=1557.7) and MeSO$_2$ ([M+H]$^+$=1611.2). The MTT group was selectively removed using 1% CF$_3$CO$_2$H in chloroform. MS analysis: R$^1$=4-methylphenylsulfonyl, [M+H]$^+$=1430.3; R$^1$=MeSO$_2$, [M+H]$^+$=1354.6; R$^1$=CN, [M+H]$^+$=1301.6. The resultant linker, shown in FIG. 7, is then reacted with PEG-(CO$_2$Su)$_4$/TFA to form the soluble conjugate of FIG. 7.

Example 11

Preparation of Amide-Linked Hydrogels

The amino-linker-octreotide(Boc) (Example 10) is allowed to react with a solution of [N$_3$-Glu(OSu)]$_4$-PEG (Example 9) to produce the amide-linked [N$_3$-Glu(linker-Octreotide(Boc))]$_4$-PEG, which is deprotected using CF$_3$CO$_2$H to provide the drug-loaded macromonomer [N$_3$-Glu(linker-Octreotide)]$_4$-PEG. A solution of this drug-loaded macromonomer is then mixed with a solution of a PEG-(cyclooctyne)$_4$ under conditions similar to those described in Ashley, et al., "Hydrogel drug delivery system with predictable and tunable drug release and degradation rates," Proc. Natl. Acad. Sci. USA (2013) 110:2318-2323 to provide a degradable hydrogel that releases octreotide at a controlled rate.

According to this general procedure, a solution containing [N$_3$-Glu(OSu)]$_4$-PEG$_{20\,kDa}$ (4.16 µmol PEG, 16.64 µmole N$_3$, 15.5 µmoles NHS, ~92% NHS loaded) in 1.3 mL acetonitrile was combined with N$^{\varepsilon 5}$-Boc N$^\alpha$-amino-linker-octreotide wherein R$^1$=MeSO$_2$ (15.8 µmoles, 21.4 mg) in 0.7 mL acetonitrile with N,N-diisopropylethyl-amine (31.6 µmol). The reaction progress was followed by size-exclusion HPLC. At completion, the HPLC trace showed two PEG species containing octreotide: 75% PEG-[octreotide]$_4$ (RV 7.9 mL) and 25% PEG-[octreotide]$_3$ (RV 7.8 mL). Unreacted octreotide equivalent to 9% of the total A$_{280}$ was also present. The unreacted NHS was capped by addition of 16.5 µmol ethanolamine. After 10 minutes the reaction pH was dropped to ~3.5 by dilution in 2.5 mL of H$_2$O containing 0.1% TFA to protect the base labile linker. The reaction was dialyzed against MeOH with one dialysate change. The retentate was dried under vacuum and triturated with 4×15 mL MTBE. The precipitated product was dried under vacuum to provide 100.0 mg of title compound, 93% yield, >99% purity by size-exclusion HPLC (mixture of 75% [octreotide]$_4$ and [octreotide]$_3$).

A solution of this drug-loaded macromonomer was mixed with a solution of PEG-(BCN)$_4$ to form the hydrogel.

Example 12
Preparation of Amide-Linked Soluble Multivalent Conjugates

The amino-linker-octreotide(Boc) (Example 10) is allowed to react with a solution of 4-armed PEG-(succinimidyl ester)$_4$ to produce the amide-linked PEG-(linker-Octreotide(Boc))$_4$, which is deprotected using CF$_3$CO$_2$H to provide the drug-loaded 4-armed PEG-(linker-Octreotide)$_4$ conjugate.

Example 13
Preparation of Dendrimeric Connector
Step 1. Boc-Lys(Boc)-NH—(CH$_2$CH$_2$O)$_3$CH$_2$CH$_2$N$_3$

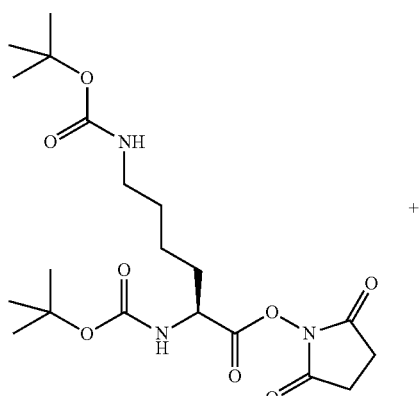

+

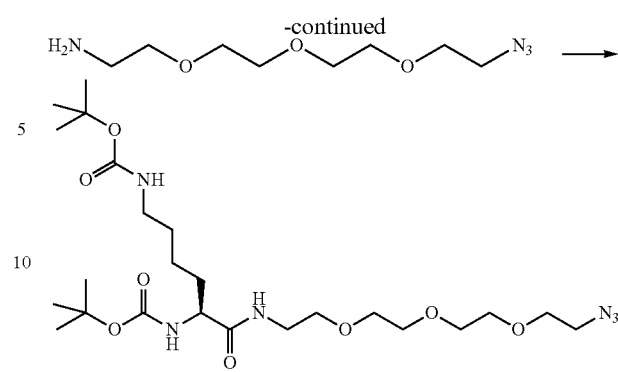

A mixture of Boc-Lys(Boc)-OSu (2.25 g, 5.1 mmol; Aldrich) and 11-azido-3,6,9-trioxaundecan-1-amine (1.0 g, 4.6 mmol; TCI) in 20 mL of CH$_2$Cl$_2$ was stirred for 2 h at ambient temperature. The mixture was diluted with CH$_2$Cl$_2$, washed with water, 5% KHSO$_4$, sat. aq. NaHCO$_3$, and brine, then dried over mgSO$_4$, filtered and evaporated. Chromatography on SiO$_2$ using a gradient of 0-50% acetone/hexane provided the product as a colorless oil (2.3 g, 4.2 mmol, 91%). HPLC (ELSD detection) showed a single peak; MS [M+H]$^+$=547.4.

Step 2. Boc-Lys(Boc)-Lys[Boc-Lys(Boc)]-NH—(CH$_2$CH$_2$O)$_3$CH$_2$CH$_2$N$_3$ 1. CF$_3$CO$_2$H/CH$_2$CL$_2$
2. Boc-Lys(Boc)-OSo Et$_3$N—CH$_3$CN

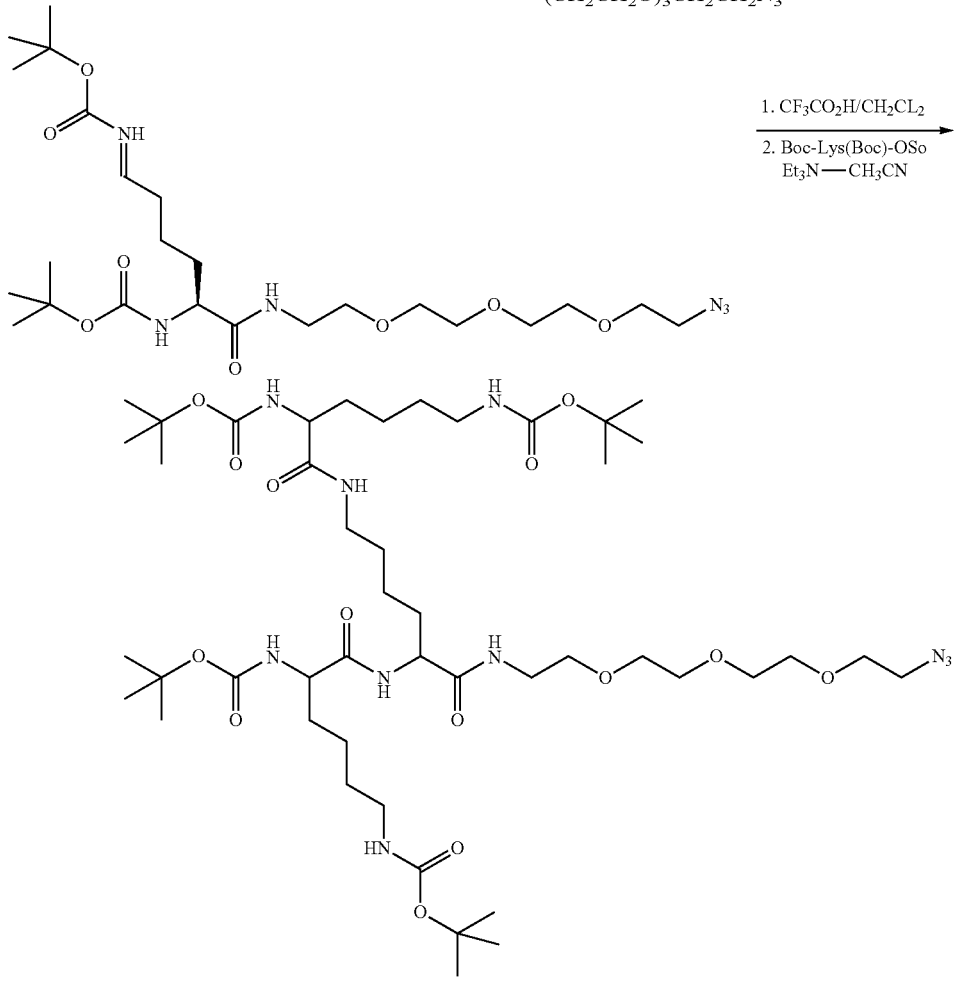

Boc-Lys(Boc)-NH—(CH$_2$CH$_2$O)$_3$CH$_2$CH$_2$N$_3$ (550 mg, 1.0 mmol) was dissolved in 5 mL of 1:1 CH$_2$Cl$_2$/CF$_3$CO$_2$H, stirred for 10 min, and evaporated. The oily residue was washed 2×10 mL of ether and dried under vacuum to provide the intermediate diamine as a colorless glass (655 mg). HPLC (ELSD detection) showed a single peak; [M+H]$^+$= 347.2.

A mixture of the diamine (280 mg, 0.5 mmol), Boc-Lys(Boc)-OSu (480 mg, 1.1 mmol), and triethylamine (0.42 mL, 3.0 mmol) in 5 mL of acetonitrile was stirred for 2 h at ambient temperature. The mixture was diluted with CH$_2$Cl$_2$, washed with water, 5% KHSO$_4$, sat. aq. NaHCO$_3$, and brine, then dried over mgSO$_4$, filtered and evaporated. Chromatography on SiO$_2$ using a gradient of 0-100% acetone/hexane provided the product as a white foam (315 mg, 0.31 mmol, 62%). HPLC (ELSD detection) showed a single peak.

Step 3. pyr-Lys(pyr)-Lys(pyr-Lys(pyr))-NH—(CH$_2$CH$_2$O)$_3$CH$_2$CH$_2$N$_3$

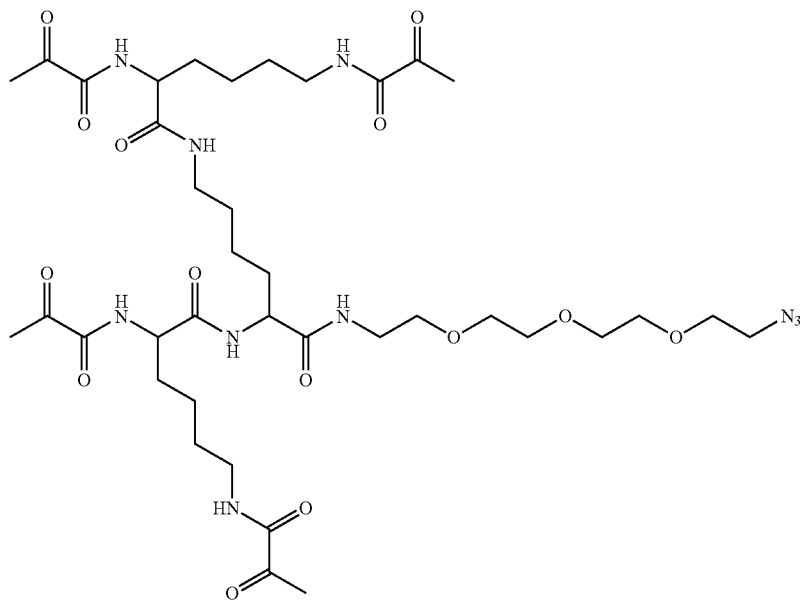 [SMILES: CC(=O)C(=O)NCCCCC(NC(=O)C(C)=O)C(=O)NCCCCC(NC(=O)C(CCCCNC(=O)C(C)=O)NC(=O)C(C)=O)C(=O)NCCOCCOCCOCCN=[N+]=[N-]]

A solution of Boc-Lys(Boc)-Lys[Boc-Lys(Boc)]-NH—(CH$_2$CH$_2$O)$_3$CH$_2$CH$_2$N$_3$ (100 mg, 0.1 mmol) in 2 mL of 1:1 CH$_2$Cl$_2$/CF$_3$CO$_2$H, stirred for 10 min, and evaporated. The oily residue was washed 2×10 mL of ether and dried under vacuum to provide the intermediate Lys-Lys(Lys)-NH—(CH$_2$CH$_2$O)$_3$CH$_2$CH$_2$N$_3$ tetra(trifluoroacetate) as a colorless glass. LC-MS [M+H]$^+$=603.4.

A solution of the Lys-Lys(Lys)-NH—(CH$_2$CH$_2$O)$_3$CH$_2$CH$_2$N$_3$ tetra(trifluoroacetate) (0.1 mmol) in 2 mL of DMF was treated with 4-nitrophenyl 2,2-diethoxypropionate (LaMattina and Muse, *J. Org. Chem.* (1987) 52:3479-3481), (150 mg, 0.53 mmol) and N,N-diisopropylethylamine (0.20 mL, 1.15 mmol) for 16 h at ambient temperature. The mix was diluted with 10 mL of water and extracted 4× with 10 mL of CH$_2$Cl$_2$. The organic extracts were combined, washed with 0.5 M Na$_2$CO$_3$, water, and brine, then dried over MgSO$_4$, filtered, and evaporated to yield a clear glass. This was dissolved in 2 mL of CH$_2$Cl$_2$ and treated with 1 mL of 50:50 CF$_3$CO$_2$H/H$_2$O for 3 h. The mix was then diluted with CH$_2$Cl$_2$ and washed with water, sat. aq. NaHCO$_3$, and brine, then dried over MgSO$_4$, filtered, and evaporated to yield the tetra-pyruvamide dendrimer as a clear glass, 119 mg.

Example 14

Preparation of Amino-Oxy-Linker-Octreotide

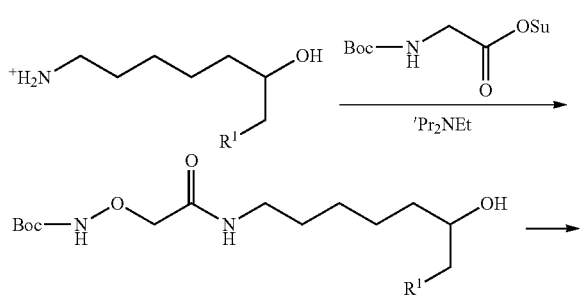

-continued

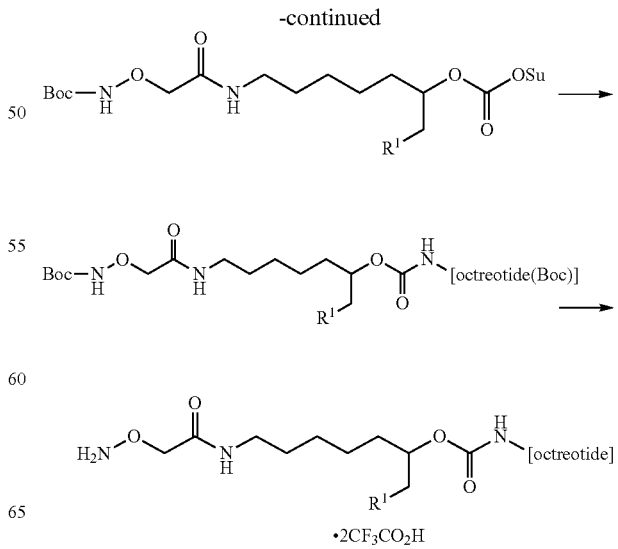

The amino linker alcohol (Example 1) is treated with 2-(Boc-aminooxy)acetic acid succinimidyl ester (1.2 eq) and DIPEA (2 eq) in $CH_2Cl_2$ to produce the intermediate Boc-aminooxy-acetamido linker alcohol. This is converted to the succinimidyl carbonate using standard procedures, first converting to the chloroformate using triphosgene/pyridine then to the succinimidyl carbonate using N-hydroxy-succinimide/pyridine (Santi, et al., *Proc. Natl. Acad. Sci. USA* (2011) 109:6211-6216). The carbonate is used to derivatize Boc-protected octreotide analogously to Example 3 and Example 4. Final treatment with 1:1 $CH_2Cl_2/CF_3CO_2H$ provides the aminooxy-linker-octreotide as the bis(trifluoroacetate) salt.

Example 15

Preparation of Dendrimeric Connector Tetra(Octreotide)

a. Preparation of [$N_a$-[7-azido-1-(N,N-bis(2-methoxyethyl)aminosulfonyl)-2-heptyloxy]carbonyl-L-lysyl]$_4$-$PEG_{20\ kDa}$: Pyridine (0.80 mL, 10 mmol) was added to a solution of 7-azido-1-(N,N-bis(2-methoxyethyl)-aminosulfonyl)-2-heptanol (1.75 g, 5.0 mmol; prepared according to the method of Santi, et al., *Proc. Natl. Acad. Sci. USA* (2011) 109:6211-6216) and triphosgene (2.5 g, 8.4 mmol) in 50 mL of anhydrous THF. After 10 min, the precipitate was removed by filtration and the filtrated was evaporated under reduced pressure. The resulting oil was dissolved in 50 mL of THF and treated with N-hydroxysuccinimide (1.15 g, 10 mmol) and pyridine (1.25 mL, 15 mmol). After 10 min, the mixture was diluted with ethyl acetate and washed with water, 5% $KHSO_4$, and brine, then dried over $MgSO_4$, filtered, and evaporated to provide the crude succinimidyl carbonate as an oil. Silica gel chromatography using a

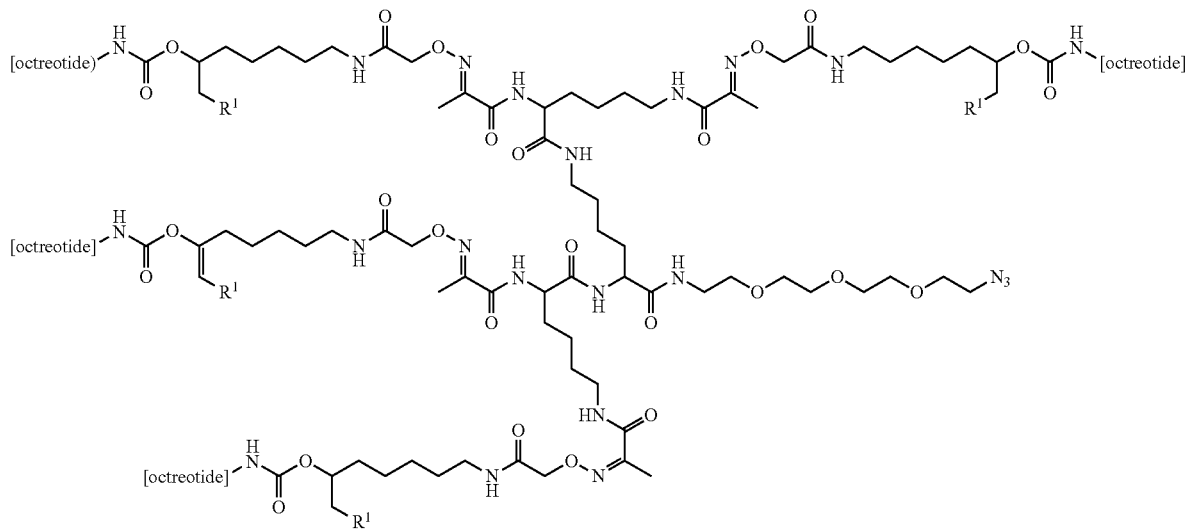

A mixture of the dendrimeric connector tetra-pyruvamide (Example 13, 1 eq) and the aminooxy-linker-octreotide (Example 14, 5 eq) in 2:1 acetonitrile/0.1 M sodium acetate, pH 3.6, is allowed to stand until oxime formation is complete.

Example 16

Preparation of Dendrimeric-Octreotide Loaded Degradable Hydrogel

Step 1. Preparation of Macromonomers.

The method for preparing the hydrogel macromonomers is illustrated using the following two compounds.

gradient of ethyl acetate/hexane gave the purified succinimidyl carbonate (1.76 g, 71%). This was dissolved in 50 mL of acetonitrile and added to a solution of $N_e$-Boc-L-lysine (1.23 g, 5.0 mmol) in 50 mL of 0.5 M $NaHCO_3$ with vigorous stirring. A clear solution was obtained after 30 min, which was concentrated to half volume, diluted with water, and washed with ethyl acetate. The aqueous phase was acidified with 6N HCl and extracted with ethyl acetate. The extract was washed with brine, then dried over $MgSO_4$, filtered, and evaporated to provide the crude $N_e$-Boc-$N_a$-[7-azido-1-(N,N-bis(2-methoxyethyl)-aminosulfonyl)-2-heptyloxy]carbonyl-L-lysine. Silica gel chromatography using a gradient of acetone/hexane gave the purified lysine derivative (1.4 g, 50%). This was dissolved in 25 mL of THF and treated with N-hydroxysuccinimide (0.27 g, 2.35 mmol) and dicyclohexylcarbodiimide (0.50 g, 2.42 mmol) at 4° C. for 24 h. The resulting suspension was filtered to provide a solution of the NHS ester in THF, a portion of which (12.5 mL, 1.12 mmol) was added to a solution of 20-kDa 4-armed PEG-tetraamine tetrahydrochloride (5.00 g, 1.0 mmol amines; JenKem Technologies) and DIPEA (0.35 mL, 2.0 mmol) in 40 mL of acetonitrile. After 2 h, a trinitrobenzenesulfonate assay indicated <1% free amines remaining. The mix was concentrated, redissolved in THF and precipitated by slow addition to 200 mL of stirred methyl t-butyl ether. The precipitate was collected and dried under vacuum to provide 5.46 g (98%) of the Boc-protected macromonomer. This material was dissolved in 25 mL of $CH_2Cl_2$, cooled on ice, and treated with 25 mL of $CF_3CO_2H$. After warming to ambient temperature, the mix was kept and additional 30 min, then concentrated, diluted with THF, and precipitated by slow addition to 200 mL of ether. The precipitate was collected, washed with ether and MTBE, then dried under vacuum to provide 5.2 g of the macromonomer.

b. Preparation of $PEG_{20\ kDa}$-$(MFCO)_4$. A mixture of 20-kDa 4-armed PEG-tetraamine tetrahydrochloride (1.7 g, 0.34 mmol amines; JenKem Technologies), DIPEA (0.12 mL, 0.69 mmol), and pentafluorophenyl 3-fluorocyclooctyne-3-carboxylate (0.40 mL of a 1 M solution in acetonitrile, 0.40 mmol) in 6 mL of acetonitrile was kept for 20 h. Any unreacted amines were then capped by addition of 32 uL of acetic anhydride. The mixture was concentrated, redissolved in 10 mL of THF and precipitated by slow addition to 100 mL of stirred methyl t-butyl ether. The precipitate was collected, washed with MTBE, and dried under vacuum to provide the second macromonomer (1.7 g).

Step 2. Preparation of Amino-Hydrogel Microspheres.

Solutions of the two macromonomers from above were prepared in 10 mM acetate, pH 5, at reactive group concentrations of 10 mM. A flow-focusing microfluidics device (Dolomite Microfluidics) was used with a continuous immiscible phase of HFE-7500 (3M Novec) containing 2% w/v FSA (RAN Biotechnologies) surfactant to mix the two macromonomer solutions in a 1:1 ratio. The resulting suspension of microspheres was concentrated by centrifugation, and the resulting paste was partitioned between 0.1% $NaN_3$ in water and a solution of 10% w/v perfluorooctanol in HFE-7500 to strip the surfactant. The microspheres were collected by centrifugation. This step was repeated, then the microspheres were washed 3× with HFE-7500 followed by 4× with water.

Step 2. Amine Derivatization.

A slurry of amino microspheres in acetonitrile (31 mg of dry microsphere/g of slurry, 675 mg slurry, 2.0 μmol $NH_2$) is added to a tared 5 mL BD luer lock syringe. Next is successively added DIPEA (1.7 μL, 10 μmol) and pentafluorophenyl 3-fluorocyclooctyne-1-carboxylate (20 mM by mass in acetonitrile, 0.20 mL, 4.0 μmol). The syringe is capped then agitated on an orbital shaker at ambient temperature overnight. $Ac_2O$ (1.9 μL, 20 μmol) and DIPEA (1.7 μL, 10 μmol) are added to cap any unreacted amines. After 1 h, the syringe is centrifuged (~3000×g, 10 min) to pellet the derivatized microspheres, and the supernatant is removed through a needle with an inline filter. The microspheres are diluted with 4 mL of acetonitrile, and the suspension incubated for 10 min. The syringe is centrifuged, and the supernatant was removed. Washing is repeated three times as described above (4 total washes×4 mL, 10 min each). The microspheres are then similarly washed with $H_2O$ (4×4 mL, 10 min each) to yield a loosely packed slurry of MFCO-derivatized microspheres.

Step 3. Loading.

A slurry of MFCO-derivatized PEG microspheres and the azido-dendrimer of Example 15 is shaken for 24 h, then the microspheres are collected by centrifugation and washed with acetonitrile to remove any unreacted azido-dendrimer.

The invention claimed is:
1. A conjugate of formula (A):
(A)
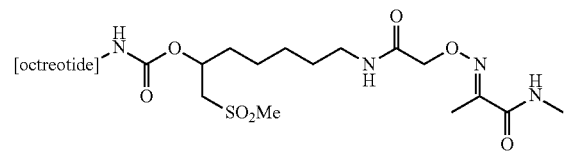
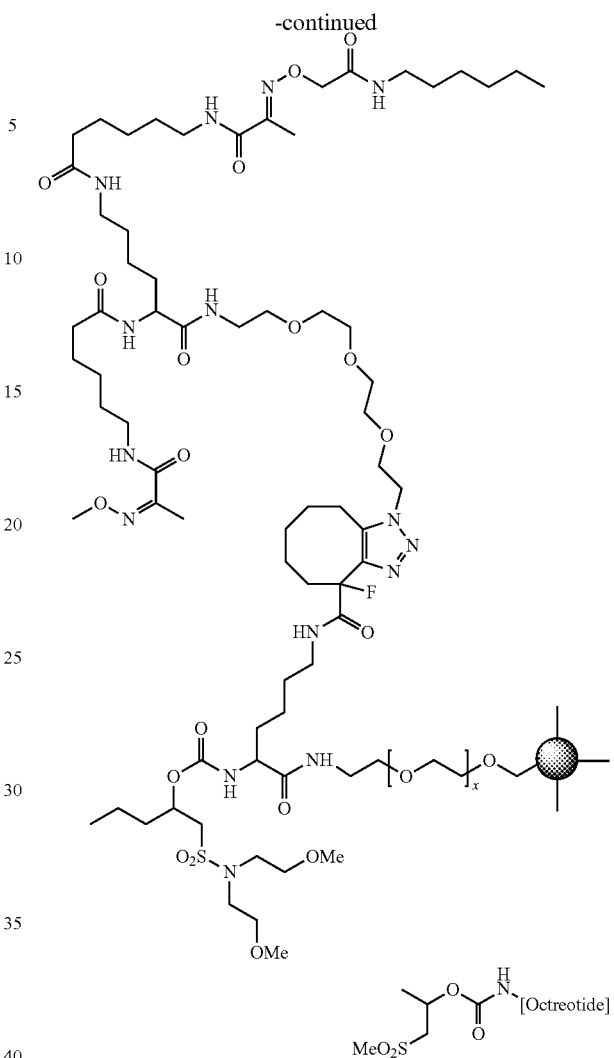
wherein the spheres represent 4 armed 20 kD PEG and the three remaining extensions shown from said spheres represent repetitions of the remainder of formula (A).
* * * * *